(12) United States Patent
Nagel et al.

(10) Patent No.: US 10,835,743 B2
(45) Date of Patent: *Nov. 17, 2020

(54) METHODS AND DEVICES FOR SURGICAL PRE-TREATMENT

(71) Applicant: VOMARIS INNOVATIONS, INC., Tempe, AZ (US)

(72) Inventors: Michael Nagel, Tempe, AZ (US); Mary Maijer, Tempe, AZ (US); Wendell King, Tempe, AZ (US); Jeffry Skiba, Tempe, AZ (US)

(73) Assignee: Vomaris Innovations, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/315,972

(22) PCT Filed: Jun. 3, 2015

(86) PCT No.: PCT/US2015/034033
§ 371 (c)(1),
(2) Date: Dec. 2, 2016

(87) PCT Pub. No.: WO2015/187858
PCT Pub. Date: Dec. 10, 2015

(65) Prior Publication Data
US 2017/0113038 A1      Apr. 27, 2017

Related U.S. Application Data

(60) Provisional application No. 62/007,295, filed on Jun. 3, 2014, provisional application No. 62/012,006, filed
(Continued)

(51) Int. Cl.
*A61N 1/00*       (2006.01)
*A61N 1/32*       (2006.01)
(Continued)

(52) U.S. Cl.
CPC .......... *A61N 1/326* (2013.01); *A61N 1/0468* (2013.01); *A61N 1/0476* (2013.01);
(Continued)

(58) Field of Classification Search
CPC .............. A61N 1/36014; A61N 1/0468; A61N 1/0476; A61N 1/0492; A61N 1/0548; A61N 1/326
See application file for complete search history.

(56) References Cited

U.S. PATENT DOCUMENTS

2005/0192636 A1    9/2005    Skiba et al.
2010/0009087 A1    1/2010    From et al.
(Continued)

OTHER PUBLICATIONS

International Search Report & Written Opinion of PCT/US2015/034033 dated Oct. 27, 2015.
(Continued)

*Primary Examiner* — Mallika D Fairchild
(74) *Attorney, Agent, or Firm* — K&L Gates LLP; Louis C. Cullman; Hal Gibson

(57) ABSTRACT

An apparatus includes multiple first reservoirs and multiple second reservoirs joined with a substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

13 Claims, 18 Drawing Sheets

Related U.S. Application Data on Jun. 13, 2014, provisional application No. 62/090,011, filed on Dec. 10, 2014, provisional application No. 62/137,987, filed on Mar. 25, 2015, provisional application No. 62/138,041, filed on Mar. 25, 2015, provisional application No. 62/153,163, filed on Apr. 27, 2015.

(51) Int. Cl.
*A61N 1/36* (2006.01)
*A61N 1/04* (2006.01)
*A61N 1/20* (2006.01)
*C12N 13/00* (2006.01)
*A61N 1/05* (2006.01)

(52) U.S. Cl.
CPC ......... *A61N 1/0492* (2013.01); *A61N 1/0548* (2013.01); *A61N 1/205* (2013.01); *A61N 1/328* (2013.01); *A61N 1/36014* (2013.01); *C12N 13/00* (2013.01); *A61N 1/0436* (2013.01); *A61N 1/0464* (2013.01); *A61N 1/0484* (2013.01)

(56) References Cited

U.S. PATENT DOCUMENTS

2011/0118655 A1* 5/2011 Fassih .................... A61N 1/205
  604/20
2014/0093832 A1  4/2014 Nemeh et al.

OTHER PUBLICATIONS

Meneheslami, "The Role of Integrins in Wound Healing", TheSicence Creative Quaterly, Aug. 2004, p. 2-3, [online]URL=<http://www.scq.ubc.ca/the-role-of-integrins-in-wound-healing/>.

* cited by examiner

METHODS AND DEVICES FOR SURGICAL PRE-TREATMENT

CROSS REFERENCE TO RELATED APPLICATIONS

This application claims benefit under 35 U.S.C. § 119(e) from U.S. Provisional Patent Application Ser. Nos. 62/007,295, filed Jun. 3, 2014; 62/012,006, filed Jun. 13, 2014; 62/090,011, filed Dec. 10, 2014; 62/137,987, filed Mar. 25, 2015; 62/138,041, filed Mar. 25, 2015; and 62/153,163, filed Apr. 27, 2015; the content of each of which is incorporated herein by reference in its entirety.

FIELD

Biologic tissues and cells are affected by a unique electrical stimulus. Accordingly, apparatus and techniques for applying electric stimulus to tissue have been developed to address a number of medical issues. The present specification relates to methods and devices useful for treatment of tissue prior to surgery or other disruption.

BACKGROUND

The skin is a natural barrier against infection; however any surgery that causes a break in the skin can lead to a postoperative infection, often described as surgical site infections (SSIs). Following surgery, the chances of developing an SSI are about 1 to 3 percent. SSIs are often one or more of three types. A "superficial incisional" SSI occurs in the area of the skin where the surgical incision was made. A "deep incisional" SSI occurs beneath the incision area in muscle tissue and in fascia, as well as the tissue surrounding the muscles. An "organ" or "space" SSI can occur in any area of the body other than the skin, muscle, or fascia that was involved in the surgery, such as an organ or between organs.

Infections after surgery are often caused by microorganisms. The most common of these include the bacteria *Staphylococcus*, *Streptococcus*, and *Pseudomonas*. Microorganisms can infect a surgical wound through various forms of contact, such as from the touch of a contaminated caregiver or surgical instrument, through microorganisms in the air, or through microorganisms that are already on or in the body. The degree of risk for an SSI is linked to the type of surgery performed—risk factors for SSIs include surgery that lasts more than two hours; advanced age, obesity, smoking, diabetes, and cancer.

SUMMARY

Embodiments disclosed herein include systems, devices, and methods for pre-treating surgical sites, for example using bioelectric devices that comprise a multi-array matrix of biocompatible microcells and a fluid such as a conductive fluid or cream, for example an antibacterial. By pre-treating surgical sites, the presence of microorganisms surrounding the surgery site can be limited or reduced. In addition, pre-treatment of the surgery site can stimulate the healing process by increasing cell migration, ATP production, and angiogenesis.

Embodiments disclosed herein comprise bioelectric devices that comprise a multi-array matrix of biocompatible microcells. Such matrices can include a first array comprising a pattern of microcells, for example formed from a first conductive solution, the solution including a metal species; and a second array comprising a pattern of microcells, for example, formed from a second conductive solution, the solution including a metal species capable of defining at least one voltaic cell for spontaneously generating at least one electrical current with the metal species of the first array when said first and second arrays are introduced to an electrolytic solution and said first and second arrays are not in physical contact with each other. Certain aspects utilize an external power source such as AC or DC power, or pulsed RF, or pulsed current, such as high voltage pulsed current. In one embodiment, the electrical energy is derived from the dissimilar metals creating a battery at each cell/cell interface, whereas those embodiments with an external power source can employ conductive electrodes in a spaced configuration to predetermine the electric field shape and strength.

Aspects disclosed herein include systems, devices, and methods for preventing damage to, repairing, and rejuvenating teeth and gums, for example using bioelectric devices that comprise a multi-array matrix of biocompatible microcells and a fluid such as a conductive fluid, or cream, or saliva.

Also disclosed herein are electroceutical fabrics.

Also disclosed herein are dressings for use with medical devices that can be inserted into the body, such as catheters.

a. Scanning Electron Microscope (SEM) image;
b. Light Microscope Image;
c. Closer view of a golden dot and a grey dot in B respectively.
d. Closer view of a golden dot and a grey dot in B respectively.
e. EDS element map of zinc;
f. EDS element map of silver;
g. EDS element map of oxygen;
h. EDS element map of carbon. Scale bar A-B, E-H: 1 mm; C-D: 250 μm
   18(B,C) Absorbance measurement on treating planktonic PAO1 culture with placebo, Ag/Zn BED and placebo+Ag dressing; and CFU measurement.
   18(D) Zone of inhibition with placebo, Ag/Zn BED and placebo+Ag dressing.

Figure 19:
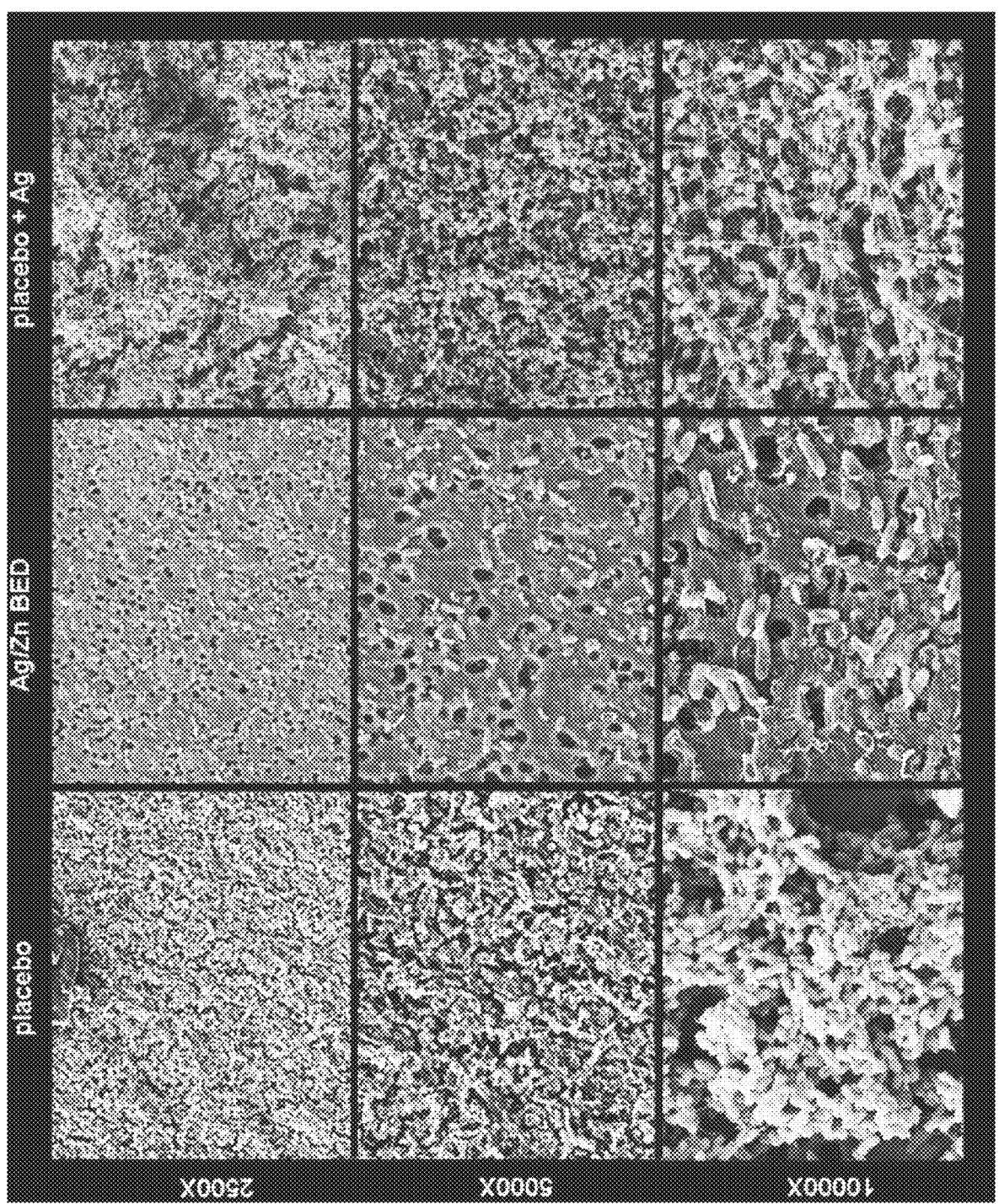

FIG. 19 depicts Scanning Electron Microscope (SEM) images of in-vitro *Pseudomonas aeruginosa* PAO1 biofilm treated with placebo, an embodiment disclosed herein ("BED"), and placebo+Ag dressing. The BED treated biofilm shows a dramatic decrease in bacteria number.

Figure 20:
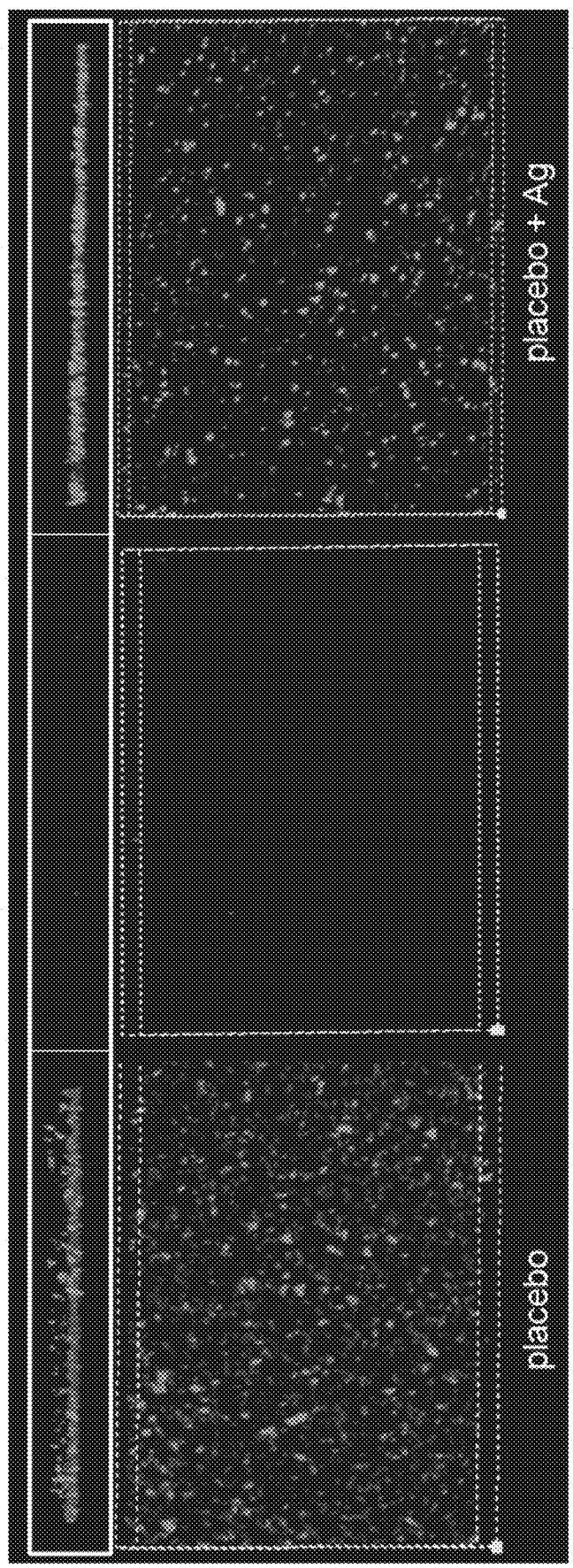

FIG. 20 shows extracellular polysaccharide staining (EPS).

Figure 21:
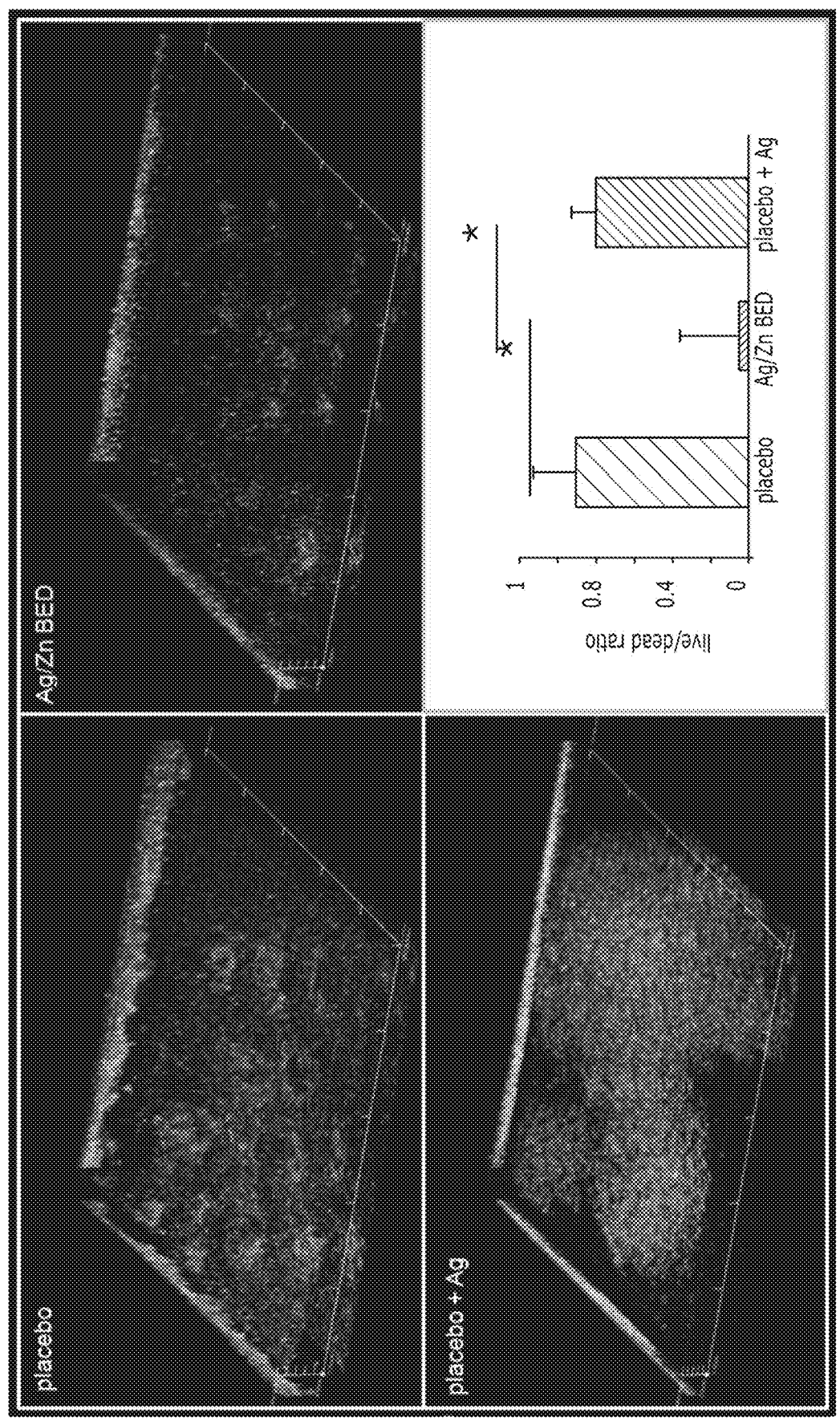

FIG. 21 shows live/dead staining. The green fluorescence indicates live PAO1 bacteria while the red fluorescence indicates dead bacteria.

Figure 22:
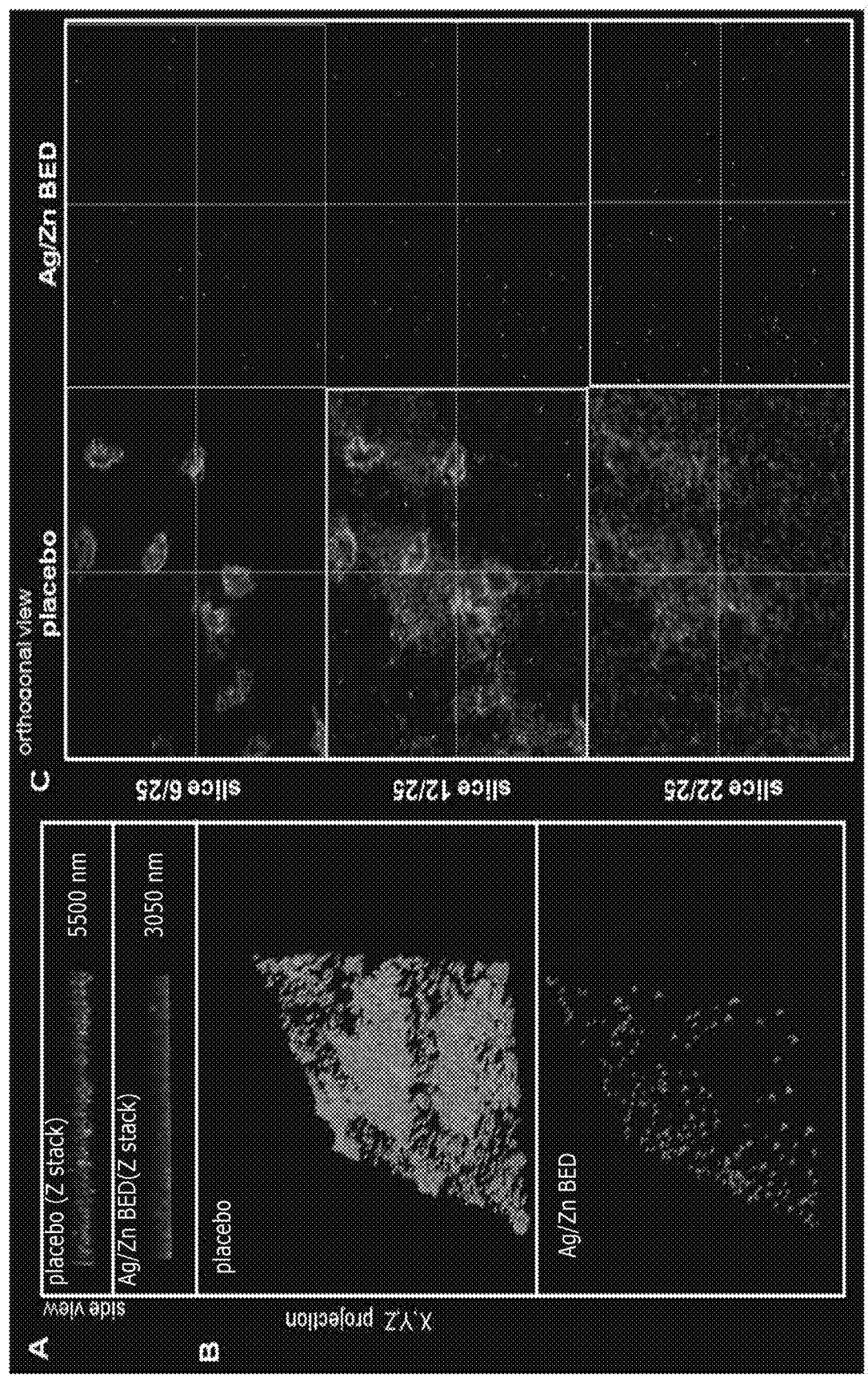

FIG. 22 shows PAO1 staining.

Figure 23:
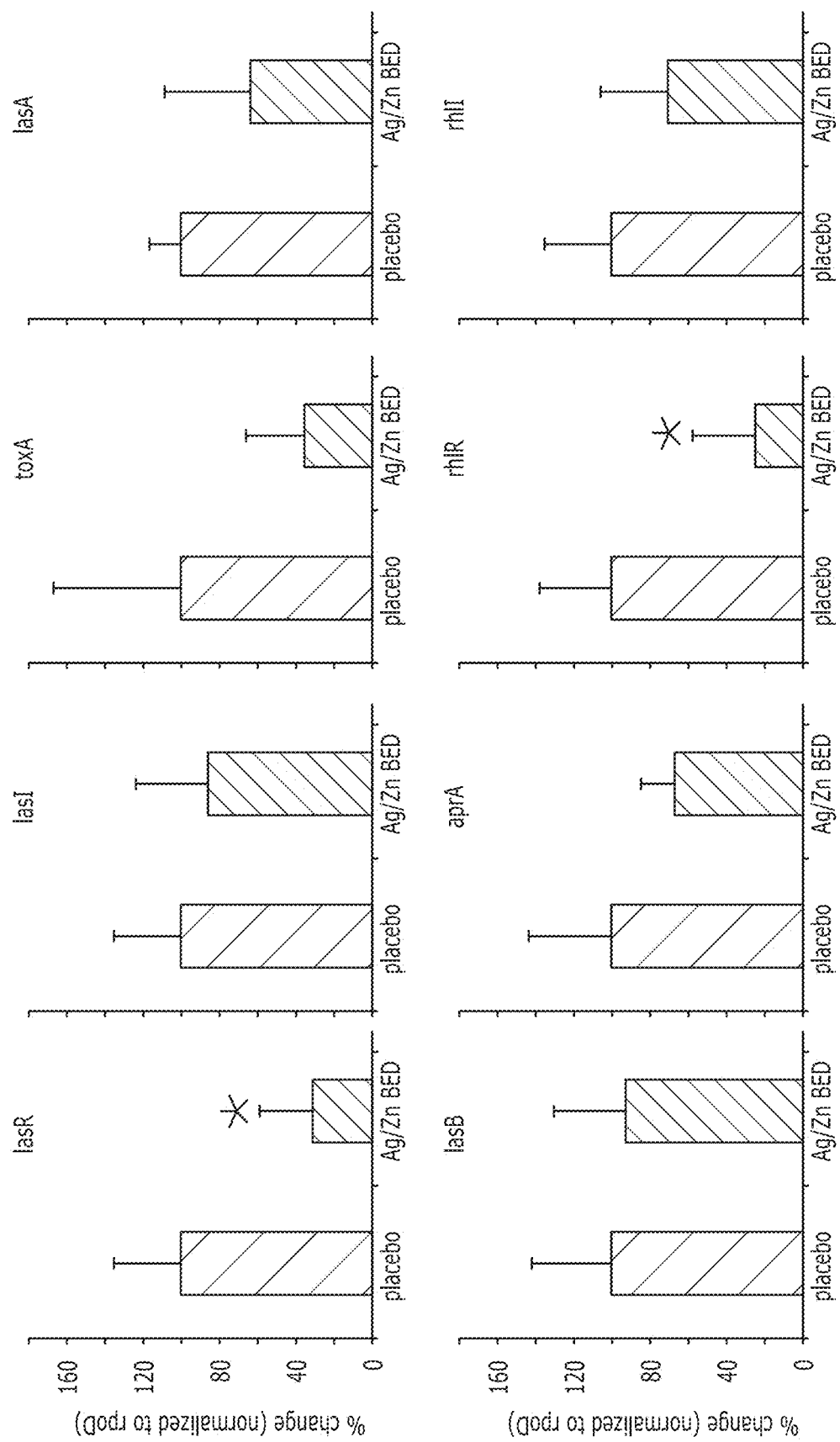

FIG. 23 depicts real-time PCR to assess quorum sensing gene expression.

Figure 24:
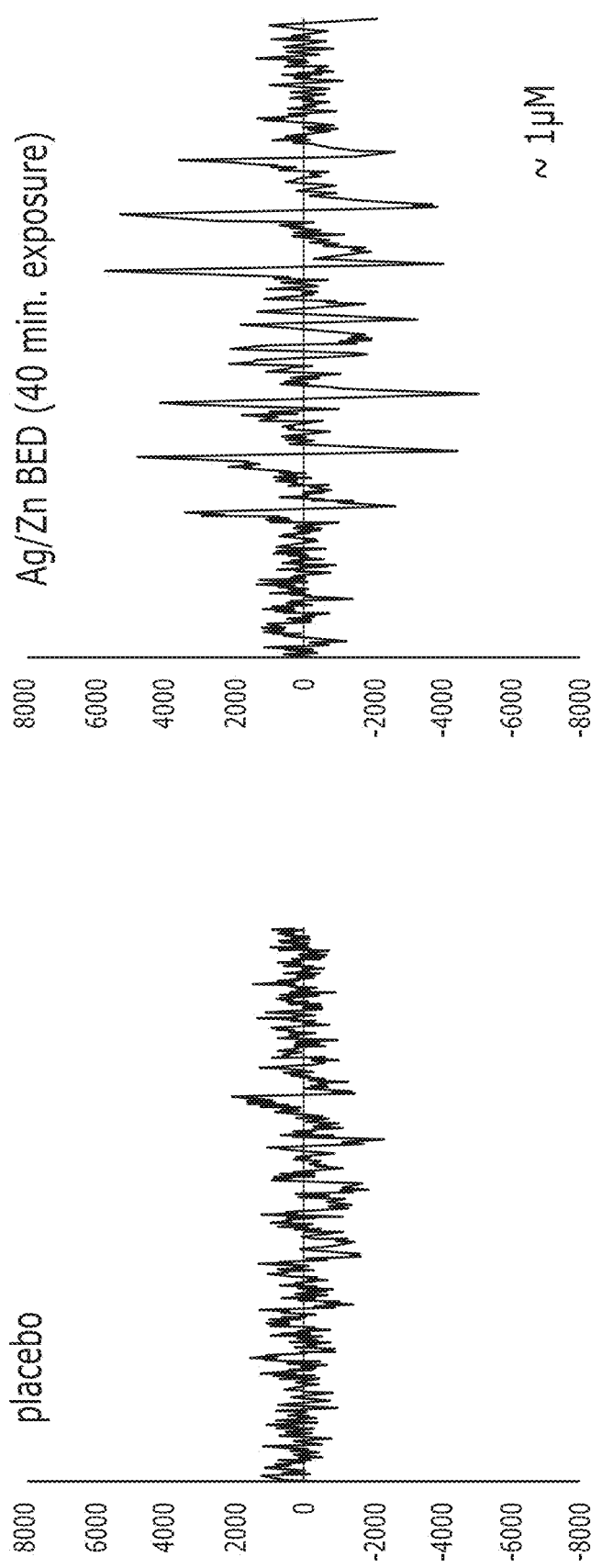

FIG. 24 shows electron paramagnetic (EPR) spectra using DEPMPO (a phosphorylated derivative of the widely used DMPO spin trap). Spin adduct generation upon exposure to disclosed embodiments for 40 minutes in PBS.

Figure 25:
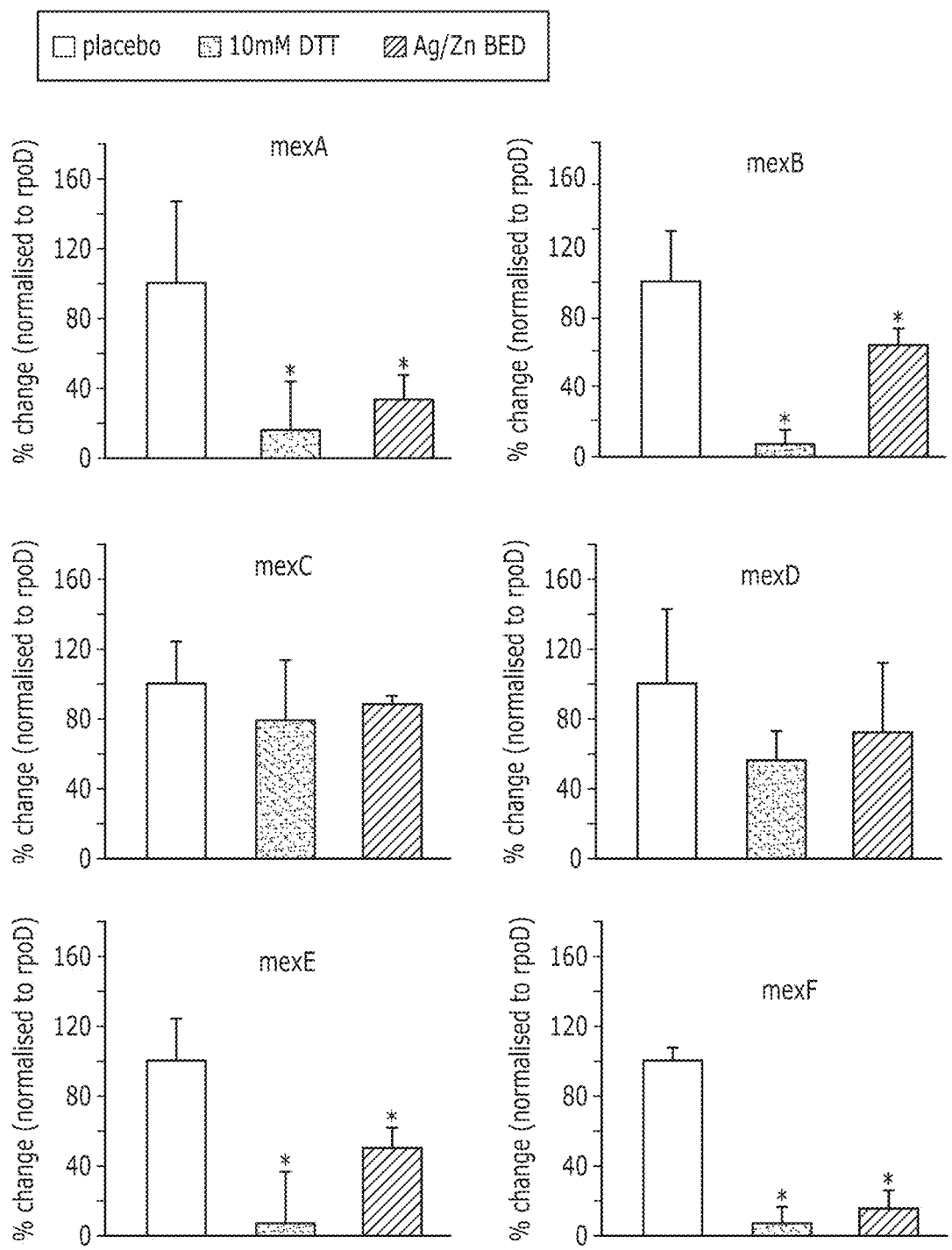

FIG. 25 depicts real-time PCR performed to assess mex gene expression upon treatment with Ag/Zn BED and 10 mM DTT.

Figure 26:
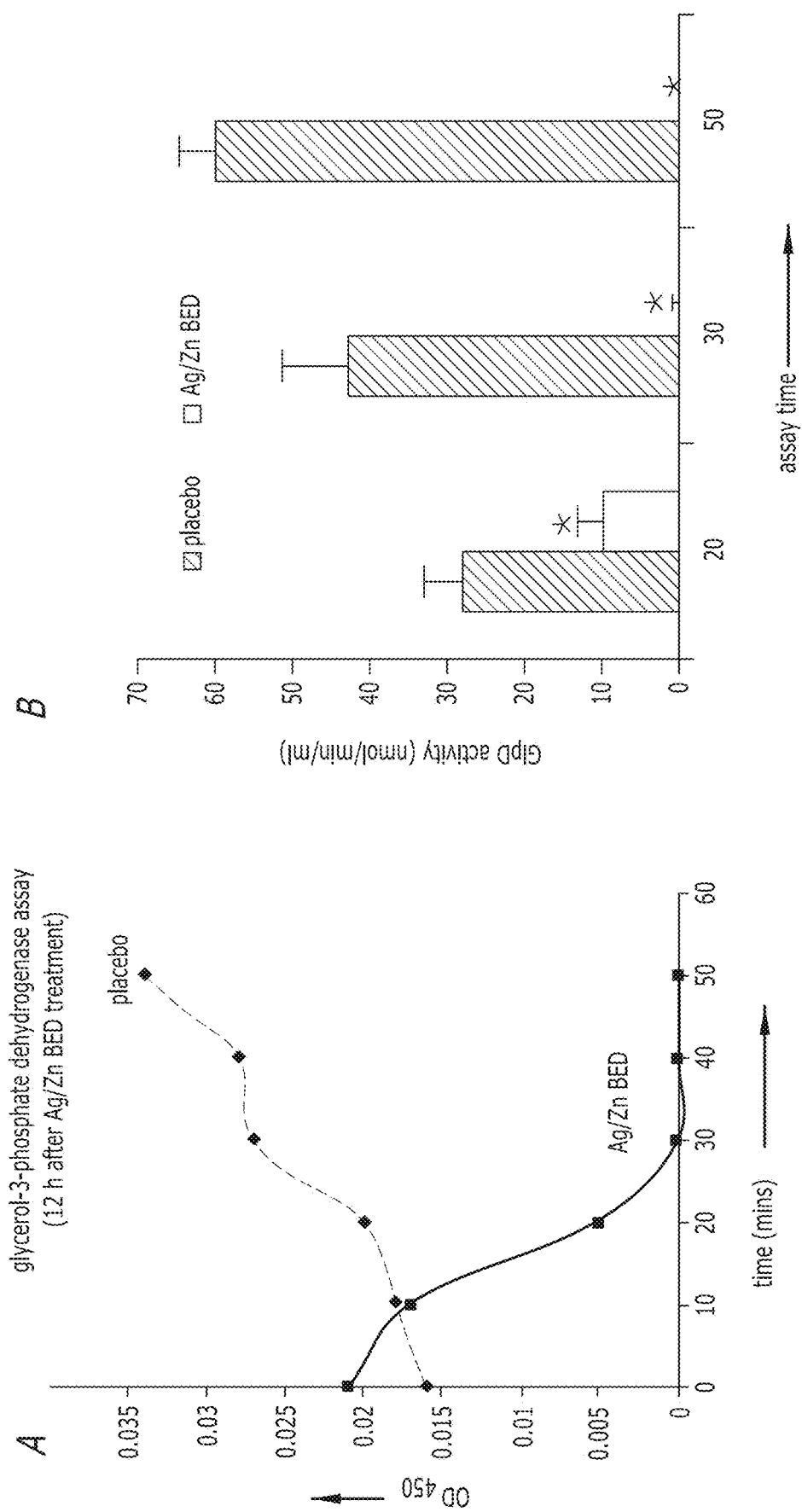

FIG. 26 shows Glycerol-3-Phosphate Dehydrogenase (GPDH) enzyme activity.
a. OD was measured in the kinetic mode.
b. GPDH activity was calculated using the formula, Glycerol-3-Phosphate dehydrogenase activity=B/($\Delta T \times$ V)×Dilution Factor=nmol/min/ml, where: B=NADH amount from Standard Curve (nmol). $\Delta T$=reaction time (min). V=sample volume added into the reaction well (ml).

DETAILED DESCRIPTION

Embodiments disclosed herein include systems and devices that can provide a low level electric field (LLEF) to a tissue or organism (thus a "LLEF system") or, when brought into contact with an electrically conducting material, can provide a low level electric micro-current (LLEC) to a tissue or organism (thus a "LLEC system"). Thus, in embodiments a LLEC system is a LLEF system that is in contact with an electrically conducting material, for example a liquid material. In certain embodiments, the micro-current or electric field can be modulated, for example, to alter the duration, size, shape, field depth, duration, current, polarity, or voltage of the system. For example, it can be desirable to employ an electric field of greater strength or depth in an area where skin is thicker to achieve optimal treatment. In embodiments the watt-density of the system can be modulated.

Definitions

"Activation gel" as used herein means a composition useful for maintaining a moist environment within and about the skin. Activation gels can be conductive. Activation gels can also be antibacterial.

"Affixing" as used herein can mean contacting a patient or tissue with a device or system disclosed herein. In embodiments "affixing" can include the use of straps, elastic, etc.

"Antibacterial agent" or "antibacterial" as used herein refers to an agent that interferes with the growth and reproduction of bacteria. Antibacterial agents are used to disinfect surfaces and eliminate potentially harmful bacteria. Unlike antibiotics, they are not used as medicines for humans or animals, but are found in products such as soaps, detergents, health and skincare products and household cleaners. Antibacterial agents may be divided into two groups according to their speed of action and residue production: The first group contains those that act rapidly to destroy bacteria, but quickly disappear (by evaporation or breakdown) and leave no active residue behind (referred to as non-residue-producing). Examples of this type are the alcohols, chlorine, peroxides, and aldehydes. The second group consists mostly of newer compounds that leave long-acting residues on the surface to be disinfected and thus have a prolonged action (referred to as residue-producing). Common examples of this group are triclosan, triclocarban, and benzalkonium chloride. As used herein, "antibacterial agent" includes sanitizers, disinfectants, and sterilizers. Antibacterials can be used to reduce the population of proliferation of bacteria, for example *Acinetobacter baumannii, Corynebacterium amycolatum, Enterobacter aerogenes, Enterococcus faecalis, Escherichia coli, Klebsiella pneumonia, Pseudomonas aeruginosa, Serratia marcescens, Staphylococcus aureus*, and *Staphylococcus epidermidis*, or the like.

"Applied" or "apply" as used herein refers to contacting a surface with a conductive material, for example printing, painting, or spraying a conductive ink on a surface. Alternatively, "applying" can mean contacting a patient or tissue or organism with a device or system disclosed herein.

"Catheter" as used herein refers to a thin tube made from medical grade materials serving a broad range of functions. Catheters are medical devices that can be inserted in the body to treat diseases or perform a surgical procedure. Catheters can be inserted into a body cavity, duct, or vessel. Functionally, they allow drainage, administration of fluids or gases, access by surgical instruments, and also perform a wide variety of other tasks depending on the type of catheter. The process of inserting a catheter is catheterization. In most uses, catheter is a thin, flexible tube ("soft" catheter) though catheters are available in varying levels of stiffness depending on the application.

"Conductive material" as used herein refers to an object or type of material which permits the flow of electric charges in one or more directions. Conductive materials can include solids such as metals or carbon, or liquids such as conductive metal solutions and conductive gels. Conductive materials can be applied to form at least one matrix. Conductive liquids can dry, cure, or harden after application to form a solid material.

"Discontinuous region" as used herein refers to a "void" in a material such as a hole, slot, or the like. The term can mean any void in the material though typically the void is of a regular shape. A void in the material can be entirely within the perimeter of a material or it can extend to the perimeter of a material.

"Disruption" or "disrupted space" as used herein refers to any break, tear, void, cut, scratch, bit, sore, wound, gum recession, open cavity, gum flap, void in gums between tooth and gum, dental extraction, cleft palate, opening caused by surgery, or the like.

"Dots" as used herein refers to discrete deposits of dissimilar reservoirs that can function as at least one battery cell. The term can refer to a deposit of any suitable size or shape, such as squares, circles, triangles, lines, etc. The term can be used synonymously with, microcells, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand.

"Galvanic cell" as used herein refers to an electrochemical cell with a positive cell potential, which can allow chemical energy to be converted into electrical energy. More particularly, a galvanic cell can include a first reservoir serving as an anode and a second, dissimilar reservoir serving as a cathode. Each galvanic cell can store chemical potential energy. When a conductive material is located proximate to a cell such that the material can provide electrical and/or ionic communication between the cell elements the chemical potential energy can be released as electrical energy. Accordingly, each set of adjacent, dissimilar reservoirs can function as a single-cell battery, and the distribution of multiple sets of adjacent, dissimilar reservoirs within the apparatus can function as a field of single-cell batteries, which in the aggregate forms a multiple-cell battery distributed across a surface. In embodiments utilizing an external power source the galvanic cell can comprise electrodes connected to an external power source, for example a battery or other power source. In embodiments that are externally-powered, the electrodes need not comprise dissimilar materials, as the external power source can define the anode and cathode. In certain externally powered embodiments, the power source need not be physically connected to the device.

"Gingivitis" as used herein refers to a non-destructive periodontal disease that is a response to bacterial biofilms that adhere to the surface of the teeth. Gingivitis manifests itself in gum tissue through swollen gums, bright red or purple gums, bleeding gums, receding gums, formation of deep pockets between teeth and gums, loose or shifting teeth, or bad breath.

"Matrix" or "matrices" as used herein refer to a pattern or patterns, such as those formed by electrodes on a surface, such as a fabric or a fiber, or the like. Matrices can be designed to vary the electric field or electric current or microcurrent generated. For example, the strength and shape of the field or current or microcurrent can be altered, or the matrices can be designed to produce an electric field(s) or current or microcurrent of a desired strength or shape.

"Oral cavity" as used herein refers to the surfaces inside the mouth, such as hard palate, soft palate, tongue, gingivae, molars, premolars, canine, incisors, frenulum of lower and upper lip, superior and inferior vestibule, inside of cheek, or any surface within the mouth. The oral cavity is comprised of many surfaces, each with large amounts of bacteria, and bacterial biofilm.

"Oral cavity device" as used herein refers to a mouth guard, mouth tray, dentures, dental bridge, dental retainer, braces, dental tray, or any type of device that can be placed within the oral cavity.

"Oral cavity repair" or "oral cavity rejuvenation" as used herein refers to any bacteria, fungus, surgery, bite, cut, abrasion, modification, gingivitis, periodontitis, or the like that is within the oral cavity that is in need of healing, soothing, restoration, rebuilding, or the like.

"Periodontitis" as used herein refers to an inflammatory disease that affects the periodontium, i.e., the tissues that surround and support the teeth. Periodontitis can be defined as an inflammation or infection that spreads from the gums (gingiva) to the ligaments and bones that support the teeth. Periodontitis can occur by build up of plaque and tartar at the base of the teeth causing swelling traps for bacteria and plaque to form between the gums and the teeth. The term "plaque" can be defined as a biofilm that develops naturally on teeth, which is formed by colonizing bacteria trying to attach themselves to the tooth's smooth surface.

"Reduction-oxidation reaction" or "redox reaction" as used herein refers to a reaction involving the transfer of one or more electrons from a reducing agent to an oxidizing agent. The term "reducing agent" can be defined in some embodiments as a reactant in a redox reaction, which donates electrons to a reduced species. A "reducing agent" is thereby oxidized in the reaction. The term "oxidizing agent" can be defined in some embodiments as a reactant in a redox reaction, which accepts electrons from the oxidized species. An "oxidizing agent" is thereby reduced in the reaction. In various embodiments a redox reaction produced between a first and second reservoir provides a current between the dissimilar reservoirs. The redox reactions can occur spontaneously when a conductive material is brought in proximity to first and second dissimilar reservoirs such that the conductive material provides a medium for electrical communication and/or ionic communication between the first and second dissimilar reservoirs. In other words, in an embodiment electrical currents can be produced between first and second dissimilar reservoirs without the use of an external battery or other power source (e.g., a direct current (DC) such as a battery or an alternating current (AC) power source such as a typical electric outlet). Accordingly, in various embodiments a system is provided which is "electrically self contained," and yet the system can be activated to produce electrical currents. The term "electrically self contained" can be defined in some embodiments as being capable of producing electricity (e.g., producing currents) without an external battery or power source. The term "activated" can be defined in some embodiments to refer to the production of electric current through the application of a radio signal of a given frequency or through ultrasound or through electromagnetic induction. In other embodiments, a system can be provided which includes an external battery or power source. For example, an AC power source can be of any wave form, such as a sine wave, a triangular wave, or a square wave. AC power can also be of any frequency such as for example 50 Hz or 60 HZ, or the like. AC power can also be of any voltage, such as for example 120 volts, or 220 volts, or the like. In embodiments an AC power source can be electronically modified, such as for example having the voltage reduced, prior to use.

"Stretchable" as used herein refers to the ability of embodiments that stretch without losing their structural integrity. That is, embodiments can stretch to accommodate irregular skin surfaces or surfaces wherein one portion of the surface can move relative to another portion.

LLEC/LLEF Systems, and Devices

In embodiments, devices disclosed herein comprise patterns of micro-batteries that create a field between each dot pair. In embodiments, the unique field is very short, e.g. in the range of physiologic electric fields. In embodiments, the direction of the electric field produced by devices disclosed herein is omnidirectional over the surface of the wound and more in line with the physiologic.

Embodiments of the LLEC or LLEF system disclosed herein can comprise electrodes or microcells. Each electrode or microcell can be or include a conductive metal. In embodiments, the electrodes or microcells can comprise any electrically-conductive material, for example, an electrically conductive hydrogel, metals, electrolytes, superconductors, semiconductors, plasmas, and nonmetallic conductors such as graphite and conductive polymers. Electrically conductive metals can include silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrode can be coated or plated with a different metal such as aluminum, gold, platinum or silver.

In certain embodiments, reservoir or electrode geometry can comprise circles, polygons, lines, zigzags, ovals, stars, or any suitable variety of shapes. This provides the ability to design/customize surface electric field shapes as well as depth of penetration. For example. In embodiments it can be desirable to employ an electric field of greater strength or depth in an area where skin is thicker to achieve optimal treatment.

Reservoir or electrode or dot sizes and concentrations can vary, as these variations can allow for changes in the properties of the electric field created by embodiments of the invention. Certain embodiments provide an electric field at about 1 Volt and then, under normal tissue loads with resistance of 100 k to 300K ohms, produce a current in the range of 10 microamperes. The electric field strength can be determined by calculating ½ the separation distance and applying it in the z-axis over the midpoint between the cell. This indicates the theoretical location of the highest strength field line.

Embodiments disclosed herein can comprise patterns of microcells. The patterns can be designed to produce an electric field, an electric current, or both, over and through tissue such as human skin. In embodiments the pattern can be designed to produce a specific size, strength, density, shape, or duration of electric field or electric current. In embodiments reservoir or dot size and separation can be altered.

In embodiments devices disclosed herein can apply an electric field, an electric current, or both, wherein the field, current, or both can be of varying size, strength, density, shape, or duration in different areas of the embodiment. In embodiments, by micro-sizing the electrodes or reservoirs, the shapes of the electric field, electric current, or both can be customized, increasing or decreasing very localized watt densities and allowing for the design of patterns of electrodes or reservoirs wherein the amount of electric field over a tissue can be designed or produced or adjusted based upon feedback from the tissue or upon an algorithm within sensors operably connected to the embodiment and a control module. The electric field, electric current, or both can be stronger in one zone and weaker in another. The electric field, electric current, or both can change with time and be modulated based on treatment goals or feedback from the tissue or patient. The control module can monitor and adjust the size, strength, density, shape, or duration of electric field or electric current based on tissue parameters. For example, embodiments disclosed herein can produce and maintain very localized electrical events. For example, embodiments disclosed herein can produce specific values for the electric field duration, electric field size, electric field shape, field depth, current, polarity, and/or voltage of the device or system.

A system or device disclosed herein and placed over tissue such as skin can move relative to the tissue. Reducing the amount of motion between tissue and device can be advantageous to pre-treatment. Slotting or placing cuts into the device can result in less friction or tension on the skin. In embodiments, use of an elastic dressing similar to the elasticity of the skin is also possible.

Devices disclosed herein can generate a localized electric field in a pattern determined by the distance and physical orientation of the cells or electrodes. Effective depth of the electric field can be predetermined by the orientation and distance between the cells or electrodes.

In embodiments the electric field can be extended, for example through the use of a hydrogel. In certain embodiments, for example treatment methods, it can be preferable to utilize AC or DC current. For example, embodiments disclosed herein can employ phased array, pulsed, square wave, sinusoidal, or other wave forms, combinations, or the like. Certain embodiments utilize a controller to produce and control power production and/or distribution to the device.

Embodiments disclosed herein comprise biocompatible electrodes or reservoirs or dots on a surface or substrate, for example a fabric, a mouth guard, a mouth tray, a dental retainer, dental bridges, dentures, or the like. Embodiments disclosed herein can be used to treat disruptions or disrupted spaces in the oral cavity. In embodiments the surface can be pliable, for example to better follow the contours of an area to be treated, such as the contour of an individual's gums or teeth. In embodiments the surface can comprise a gauze or mesh or plastic. In embodiments the system comprises a component such as velcro, gecko glue, or, adhesives that are water resistant, or other types of attachment component to maintain or help maintain its position in or around the oral cavity device, for example, a mouth guard, mouth tray, dental retainer, dental bridge, dentures, dental tray, or the like. In further embodiments the mouth guard, mouth tray, dental retainer, dental bridge, dentures, dental tray or the like can comprise a conductive material, for example a wire to electrically link the device with other components, such as monitoring equipment or a power source. In embodiments the device can be wirelessly linked to monitoring or data collection equipment, for example linked via Bluetooth to a cell phone that collects data from the device. In certain embodiments the device can comprise data collection means, such as temperature, pressure, or conductivity data collection. In embodiments the device can be shaped to fit an area of desired use, for example the upper gums, the lower gums, the roof of the oral cavity, the bottom of the oral cavity, or any area where gum repair or rejuvenation is desired. For example, in embodiments the device can be shaped to fit any type of mouth size or shape that varies from subject to subject. In embodiments the device can be shaped to fit an area of desired use, for example primary teeth, permanent teeth, maxillary teeth, mandibular teeth, incisors, canines, premolars, molars or any area where teeth repair and rejuvenation is desired. In embodiments the device can be a two, three, four, or the like part paste that when mixed creates a LLEC or LLEF on the subjects teeth and gums. In embodiments the paste can be for example, tooth paste, dental cream, or the like. The paste can react or activate when combined together, or when subjected to saliva, hydrogel, or the like. In embodiments the device can be a two, three, four, or the like part paste that does not mix together, but is separated by the subjects teeth, gums, or the like and creates a LLEC or LLEF on the subjects oral cavity. In embodiments the paste can be for example, tooth paste, dental cream, or the like. The paste can react or activate when the parts are in close proximity with each other or touching, and subjected to saliva, hydrogel, or the like.

Embodiments can include coatings on the surface, such as, for example, over or between the electrodes or cells. Such coatings can include, for example, silicone, and electrolytic mixture, hypoallergenic agents, drugs, biologics, stem cells, skin substitutes, cosmetic products, combinations, or the like. Drugs suitable for use with embodiments of the invention include analgesics, antibiotics, anti-inflammatories, or the like.

In embodiments the material can include a port to access the interior of the material, for example to add fluid, gel, cosmetic products, a hydrating material, or some other material to the dressing. Certain embodiments can comprise a "blister" top that can enclose a material such as an antibacterial. In embodiments the blister top can contain a material that is released into or on to the material when the blister is pressed, for example a liquid or cream. For example, embodiments disclosed herein can comprise a blister top containing an antibacterial or the like. Embodiments can change color when activated, for example when producing an electric current.

In embodiments the system comprises a component such as elastic to maintain or help maintain its position. In embodiments the system comprises components such as straps to maintain or help maintain its position. In certain embodiments the system or device comprises a strap on either end of the long axis, or a strap linking on end of the long axis to the other. In embodiments that straps can comprise velcro or a similar fastening system. In embodiments the straps can comprise elastic materials. In further embodiments the strap can comprise a conductive material, for example a wire to electrically link the device with other components, such as monitoring equipment or a power source. In embodiments the device can be wirelessly linked to monitoring or data collection equipment, for example linked via Bluetooth to a cell phone or computer that collects data from the device. In certain embodiments the device can comprise data collection means, such as temperature, pH, pressure, or conductivity data collection means.

In embodiments the system comprises a component such as an adhesive or straps to maintain or help maintain its position. The adhesive component can be covered with a protective layer that is removed to expose the adhesive at the time of use. In embodiments the adhesive can comprise, for example, sealants, such as hypoallergenic sealants, gecko sealants, mussel sealants, waterproof sealants such as epoxies, and the like. Straps can include velcro or similar materials to aid in maintaining the position of the device.

In embodiments the positioning component can comprise an elastic film with an elasticity, for example, similar to that of skin, or greater than that of skin, or less than that of skin. In embodiments, the LLEC or LLEF system can comprise a laminate where layers of the laminate can be of varying elasticities. For example, an outer layer may be highly elastic and an inner layer in-elastic or less elastic. The in-elastic layer can be made to stretch by placing stress relieving discontinuous regions or slits through the thickness of the material so there is a mechanical displacement rather than stress that would break the fabric weave before stretching would occur. In embodiments the slits can extend completely through a layer or the system or can be placed where expansion is required. In embodiments of the system the slits do not extend all the way through the system or a portion of the system such as the substrate. In embodiments the discontinuous regions can pass halfway through the long axis of the substrate.

In embodiments the device can be shaped to fit an area of desired use, for example a subject's face, or around a subject's eyes, or around a subject's forehead, a subject's cheeks, a subject's chin, a subject's back, a subject's chest, a subject's nose, or any area where surgical pre-treatment is desired. For example, in embodiments the device can be shaped to fit an area where a surgical incision will be made.

Embodiments disclosed herein comprise biocompatible electrodes or reservoirs or dots on a surface or substrate, for example a fabric, a fiber, or the like. In embodiments the surface can be pliable, for example to better follow the contours of an area to be treated, such as the face or back. In embodiments the surface can comprise a gauze or mesh or plastic. Suitable types of pliable surfaces for use in embodiments disclosed herein can be absorbent or non-absorbent textiles, low-adhesives, vapor permeable films, hydrocolloids, hydrogels, alginates, foams, foam-based materials, cellulose-based materials including Kettenbach fibers, hollow tubes, fibrous materials, such as those impregnated with anhydrous/hygroscopic materials, beads and the like, or any suitable material as known in the art. In embodiments the pliable material can form, for example, a mask, such as that worn on the face, an eye patch, a shirt or a portion thereof, for example an elastic or compression shirt, or a portion thereof, a wrapping, towel, cloth, fabric, or the like. Multi layer embodiments can include, for example, a skin-contacting layer, a hydration layer, and a hydration containment layer.

An electroceutical fabric can be produced by weaving fibers wherein sections of the fibers are coated or treated with materials capable of producing electricity and forming a battery in the presence of an electrolyte.

In embodiments, the fabric can be woven of at least two types of fibers; fibers comprising sections treated or coated with a substance capable of forming a positive electrode; and fibers comprising sections treated or coated with a substance capable of forming a negative electrode. The fabric can further comprise fibers that do not form an electrode. Long lengths of fibers can be woven together to form fabrics. For example, the fibers can be woven together to form a regular pattern of positive and negative electrodes.

Figure 14:
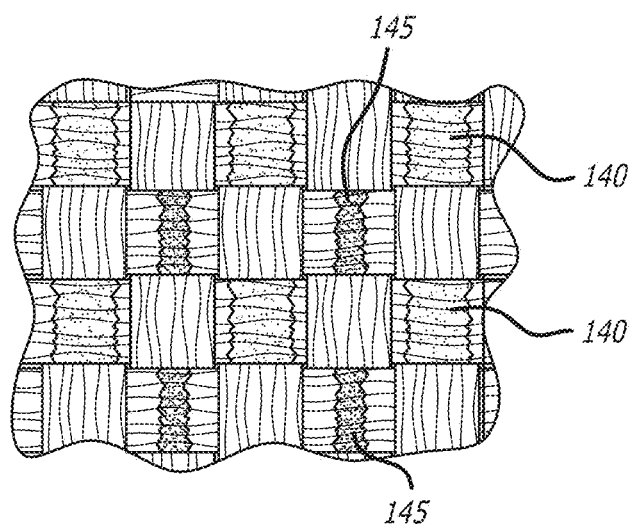
FIG. 14 depicts an electroceutical fabric as described herein.

In an embodiment, fibers are produced with discrete sections coated at regular intervals with silver (as seen in FIG. 14; discrete sections 140). Fibers are produced with discrete sections coated at regular intervals with zinc (as seen in FIG. 14; discrete sections 145). The fibers can be coated with, for example, a printer, such as a laser or ink-jet printer. In embodiments the fibers can be spray-coated. In embodiments the fibers can be dip-coated.

In embodiments, continuous fibers can be produced with sections of the fiber coated with zinc. In embodiments, continuous fibers can be produced with sections of the fiber coated with silver.

Embodiments can comprise a moisture-sensitive component that changes color when the device is activated and producing an electric current.

Figure 2:
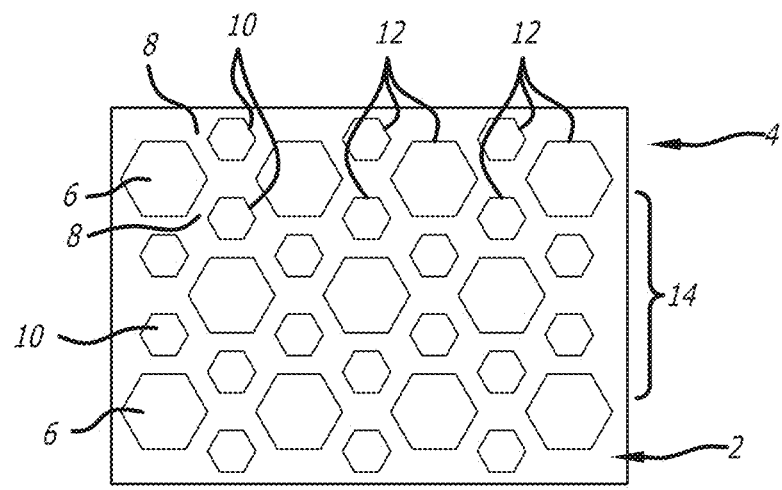
FIG. 2 is a detailed plan view of a pattern of applied electrical conductors in accordance with an embodiment disclosed herein.

In embodiments, the fibers can be woven into a pattern (as seen in FIG. 2) to produce fabric. In embodiments, the fabric can be hydrated, for example with an electrolyte, to produce a voltage between the electrodes.

Embodiments disclosed herein or produced by the methods disclosed herein can comprise "anchor" regions or "arms" or straps to affix the system securely. The anchor regions or arms can anchor the LLEC system. For example, a LLEC system can be secured to an area proximal to a joint or irregular skin surface, and anchor regions of the system can extend to areas of minimal stress or movement to securely affix the system. Further, the LLEC system can reduce stress on an area, for example by "countering" the physical stress caused by movement.

In embodiments the LLEC or LLEF system can comprise additional therapeutic materials.

In embodiments, the LLEC or LLEF system can comprise instructions or directions on how to place the system to maximize its performance.

A LLEC or LLEF system disclosed herein can comprise "anchor" regions or "arms" or straps to affix the system securely. The anchor regions or arms can anchor the LLEC or LLEF system. For example, a LLEC or LLEF system can be secured to an area proximal to a joint or irregular skin surface, and anchor regions of the system can extend to areas of minimal stress or movement to securely affix the system. Further, the LLEC system can reduce stress on an area, for example by "countering" the physical stress caused by movement.

In embodiments the LLEC or LLEF system can comprise additional materials to aid in treatment.

Embodiments can include devices in the form of a gel, such as, for example, a one- or two-component gel that is mixed on use. Embodiments can include devices in the form of a spray, for example, a one- or two-component spray that is mixed on use.

In embodiments, the LLEC or LLEF system can comprise instructions or directions on how to place the system to maximize its performance. Embodiments include a kit comprising an LLEC or LLEF system and directions for its use.

In certain embodiments dissimilar metals can be used to create an electric field with a desired voltage. In certain embodiments the pattern of reservoirs can control the watt density and shape of the electric field.

Certain embodiments can utilize a power source to create the electric current, such as a battery or a micro-battery. The power source can be any energy source capable of generating a current in the LLEC system and can include, for example, AC power, DC power, radio frequencies (RF) such as pulsed RF, induction, ultrasound, and the like.

Dissimilar metals used to make a LLEC or LLEF system disclosed herein can be silver and zinc, and the electrolytic solution can include sodium chloride in water. In certain embodiments the electrodes are applied onto a non-conductive surface to create a pattern, most preferably an array or multi-array of voltaic cells that do not spontaneously react until they contact an electrolytic solution. Sections of this description use the terms "printing" with "ink," but it is to be understood that the patterns may also be "painted" with "paints." The use of any suitable means for applying a conductive material is contemplated. In embodiments "ink" or "paint" can comprise any solution suitable for forming an electrode on a surface such as a conductive material including a conductive metal solution. In embodiments "printing" or "painted" can comprise any method of applying a solution to a material upon which a matrix is desired.

A preferred material to use in combination with silver to create the voltaic cells or reservoirs of disclosed embodiments is zinc. Zinc has been well-described for its uses in prevention of infection in such topical antibacterial agents as Bacitracin zinc, a zinc salt of Bacitracin. Zinc is a divalent cation with antibacterial properties of its own.

Figure 1:
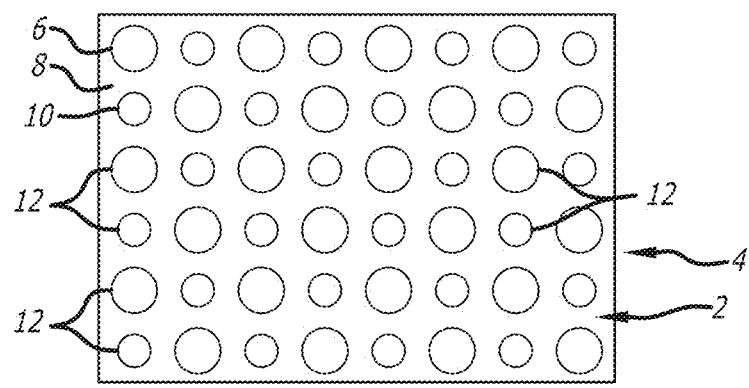
FIG. 1 is a detailed plan view of an embodiment disclosed herein.

Turning to the figures, in FIG. 1, the dissimilar first electrode 6 and second electrode 10 are applied onto a desired primary surface 2 of an article 4, for example a fabric. In one embodiment a primary surface is a surface of a LLEC or LLEF system that comes into direct contact with an area to be treated such as a skin surface.

In various embodiments the difference of the standard potentials of the electrodes or dots or reservoirs can be in a range from about 0.05 V to approximately about 5.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, 4.4 V, 4.5 V, about 4.6 V, about 4.7 V, 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, or the like.

In embodiments, LLEC systems disclosed herein can produce a low level micro-current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, or the like.

In embodiments, LLEC systems disclosed herein can produce a low level micro-current of between for example about 1 and about 400 micro-amperes, between about 20 and about 380 micro-amperes, between about 400 and about 360 micro-amperes, between about 60 and about 340 micro-amperes, between about 80 and about 320 micro-amperes, between about 100 and about 3000 micro-amperes, between about 120 and about 280 micro-amperes, between about 140 and about 260 micro-amperes, between about 160 and about 240 micro-amperes, between about 180 and about 220 micro-amperes, or the like.

In embodiments, LLEC systems disclosed herein can produce a low level micro-current about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, or the like.

In embodiments, the disclosed LLEC systems can produce a low level micro-current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, or the like.

In embodiments, LLEC systems disclosed herein can produce a low level micro-current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, or the like.

The applied electrodes or reservoirs or dots can adhere or bond to the primary surface 2 because a biocompatible binder is mixed, in embodiments into separate mixtures, with each of the dissimilar metals that will create the pattern of voltaic cells, in embodiments. Most inks are simply a carrier, and a binder mixed with pigment. Similarly, conductive metal solutions can be a binder mixed with a conductive element. The resulting conductive metal solutions can be used with an application method such as screen printing to apply the electrodes to the primary surface in predetermined patterns. Once the conductive metal solutions dry and/or cure, the patterns of spaced electrodes can substantially maintain their relative position, even on a flexible material such as that used for a LLEC or LLEF system. To make a limited number of the systems of an embodiment disclosed herein, the conductive metal solutions can be hand applied onto a common adhesive bandage so that there is an array of alternating electrodes that are spaced about a millimeter apart on the primary surface of the bandage. The solution can be allowed to dry before being applied to a surface so that the conductive materials do not mix, which could interrupt the array and cause direct reactions that will release the elements.

In certain embodiments that utilize a poly-cellulose binder, the binder itself can have an beneficial effect such as reducing the local concentration of matrix metallo-proteases through an iontophoretic process that drives the cellulose into the surrounding tissue. This process can be used to electronically drive other components such as drugs into the surrounding tissue.

The binder can include any biocompatible liquid material that can be mixed with a conductive element (preferably metallic crystals of silver or zinc) to create a conductive solution which can be applied as a thin coating to a surface. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.999%) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution. For better quality control and more consistent results, most of the crystals used should be larger than 325 mesh and smaller than 200 mesh. For example the crystals used should be between 200 mesh and 325 mesh, or between 210 mesh and 310 mesh, between 220 mesh and 300 mesh, between 230 mesh and 290 mesh, between 240 mesh and 280 mesh, between 250 mesh and 270 mesh, between 255 mesh and 265 mesh, or the like.

Other powders of metal can be used to make other conductive metal solutions in the same way as described in other embodiments.

The size of the metal crystals, the availability of the surface to the conductive fluid and the ratio of metal to binder affects the release rate of the metal from the mixture. When COLORCON® polyacrylic ink is used as the binder, about 10 to 40 percent of the mixture should be metal for a longer term bandage (for example, one that stays on for about 10 days). For example, for a longer term LLEC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, then the release rate will be much faster and a typical system will only be effective for a few days. For example, for a shorter term device, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

For LLEC or LLEF systems comprising a pliable substrate it can be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

To maximize the number of voltaic cells, in various embodiments, a pattern of alternating silver masses or electrodes or reservoirs and zinc masses or electrodes or reservoirs can create an array of electrical currents across the primary surface. A basic pattern, shown in FIG. 1, has each mass of silver equally spaced from four masses of zinc, and has each mass of zinc equally spaced from four masses of silver, according to an embodiment. The first electrode 6 is separated from the second electrode 10 by a spacing 8. The designs of first electrode 6 and second electrode 10 are simply round dots, and in an embodiment, are repeated. Numerous repetitions 12 of the designs result in a pattern. For an exemplary device comprising silver and zinc, each silver design preferably has about twice as much mass as each zinc design, in an embodiment. For the pattern in FIG. 1, the silver designs are most preferably about a millimeter from each of the closest four zinc designs, and vice-versa. The resulting pattern of dissimilar metal masses defines an array of voltaic cells when introduced to an electrolytic solution. Further disclosure relating to methods of producing micro-arrays can be found in U.S. Pat. No. 7,813,806 entitled CURRENT PRODUCING SURFACE FOR TREATING BIOLOGIC TISSUE issued Oct. 12, 2010, which is incorporated by reference in its entirety.

A dot pattern of masses like the alternating round dots of FIG. 1 can be preferred when applying conductive material onto a flexible material, such as those used for a facial or eye mask, or an article of clothing such as a shirt or shorts, as the dots won't significantly affect the flexibility of the material. To maximize the density of electrical current over a primary surface the pattern of FIG. 2 can be used. The first electrode 6 in FIG. 2 is a large hexagonally shaped dot, and the second electrode 10 is a pair of smaller hexagonally shaped dots that are spaced from each other. The spacing 8 that is between the first electrode 6 and the second electrode 10 maintains a relatively consistent distance between adjacent sides of the designs. Numerous repetitions 12 of the designs result in a pattern 14 that can be described as at least one of the first design being surrounded by six hexagonally shaped dots of the second design.

Figure 3:
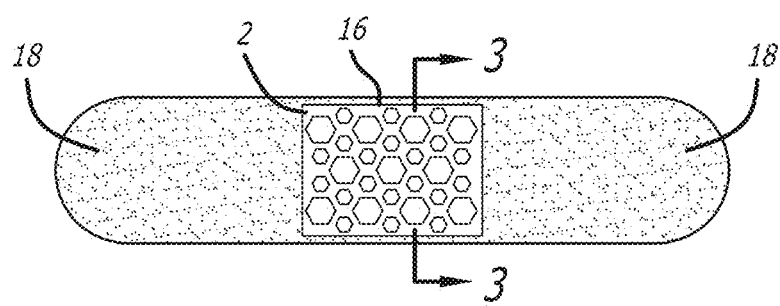
FIG. 3 is an embodiment using the applied pattern of FIG. 2.
Figure 4:
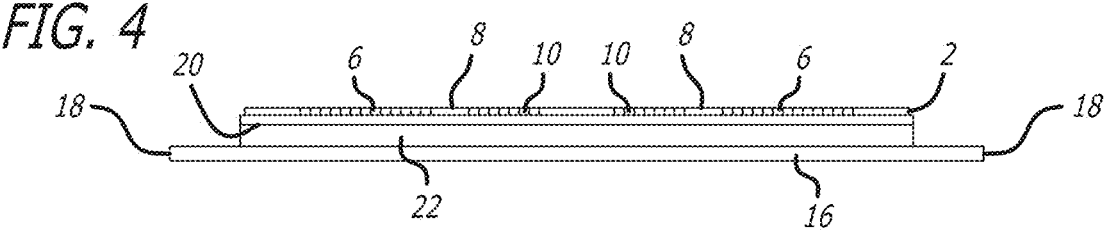
FIG. 4 is a cross-section of FIG. 3 through line 3-3.

FIGS. 3 and 4 show how the pattern of FIG. 2 can be used to make an embodiment disclosed herein. The pattern shown in detail in FIG. 2 is applied to the primary surface 2 of an embodiment. The back 20 of the printed material is fixed to a substrate layer 22. This layer is adhesively fixed to a pliable layer 16.

Figure 5:
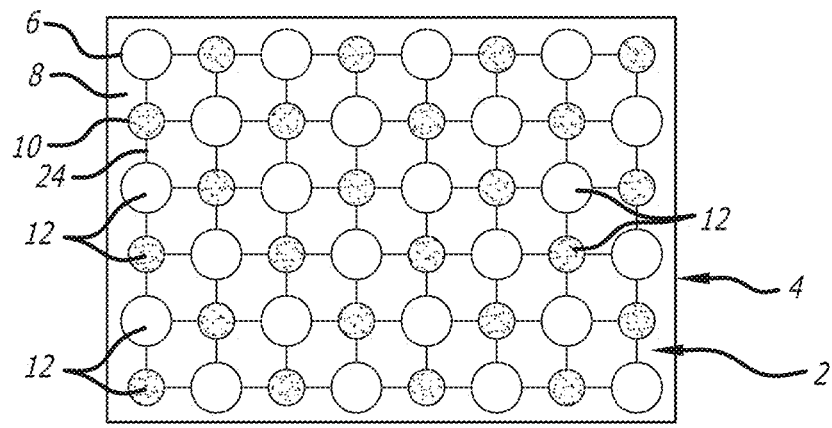
FIG. 5 is a detailed plan view of an alternate embodiment disclosed herein which includes fine lines of conductive metal solution connecting electrodes.

FIG. 5 shows an additional feature, which can be added between designs, that can initiate the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the LLEC system will be effective. If the electrolytic solution is highly conductive when the system is initially applied the fine line can be quickly depleted and the device will function as though the fine line had never existed.

Figure 6:
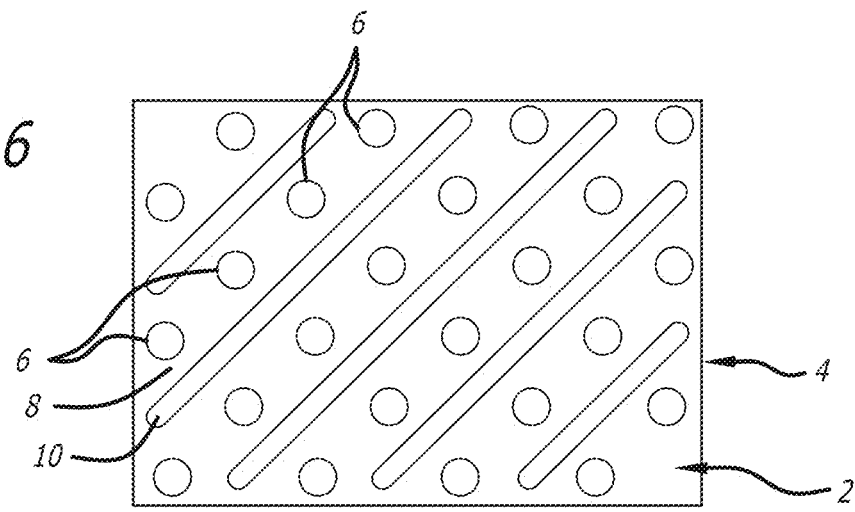
FIG. 6 is a detailed plan view of another alternate embodiment having a line pattern and dot pattern.
Figure 7:
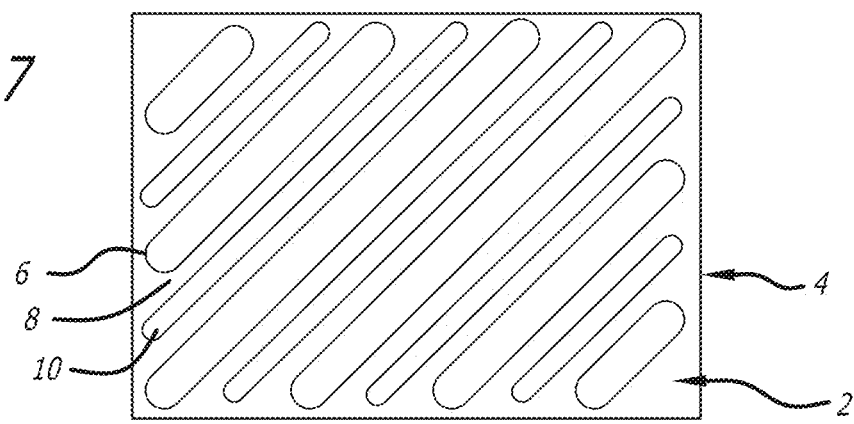
FIG. 7 is a detailed plan view of yet another alternate embodiment having two line patterns.

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that contacts a conductive fluid such as a cosmetic cream can create approximately 1 volt of potential that will penetrate substantially through the dermis and epidermis. Closer spacing of the dots can decrease the resistance, providing less potential, and the current will not penetrate as deeply. If the spacing falls below about one tenth of a millimeter a benefit of the spontaneous reaction is that which is also present with a direct reaction; silver can be electrically driven into the skin. Therefore, spacing between the closest conductive materials can be, for example, 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials can be not more than 0.1 mm, or not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 0.1 mm, or not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Disclosures of the present specification include LLEC or LLEF systems comprising a primary surface of a pliable material wherein the pliable material is adapted to be applied to an area of tissue such as the face of a subject; a first electrode design formed from a first conductive liquid that includes a mixture of a polymer and a first element, the first conductive liquid being applied into a position of contact with the primary surface, the first element including a metal species, and the first electrode design including at least one dot or reservoir, wherein selective ones of the at least one dot or reservoir have approximately a 1.5 mm+/−1 mm mean diameter; a second electrode design formed from a second conductive liquid that includes a mixture of a polymer and a second element, the second element including a different metal species than the first element, the second conductive liquid being printed into a position of contact with the primary surface, and the second electrode design including at least one other dot or reservoir, wherein selective ones of the at least one other dot or reservoir have approximately a 2.5 mm+/−2 mm mean diameter; a spacing on the primary surface that is between the first electrode design and the second electrode design such that the first electrode design does not physically contact the second electrode design, wherein the spacing is approximately 1.5 mm+/−1 mm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter of 0.2 mm, or 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

In further embodiments, electrodes, dots or reservoirs can have a mean diameter of not less than 0.2 mm, or not less than 0.3 mm, not less than 0.4 mm, not less than 0.5 mm, not less than 0.6 mm, not less than 0.7 mm, not less than 0.8 mm, not less than 0.9 mm, not less than 1.0 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2.0 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3.0 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4.0 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5.0 mm, or the like.

In further embodiments, electrodes, dots or reservoirs can have a mean diameter of not more than 0.2 mm, or not more than 0.3 mm, not more than 0.4 mm, not more than 0.5 mm, not more than 0.6 mm, not more than 0.7 mm, not more than 0.8 mm, not more than 0.9 mm, not more than 1.0 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2.0 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3.0 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4.0 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5.0 mm, or the like.

The material concentrations or quantities within and/or the relative sizes (e.g., dimensions or surface area) of the first and second reservoirs can be selected deliberately to achieve various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material. Further disclosure relating to producing reservoirs that are configured to sustain one or more currents for an approximate pre-determined period of time can be found in U.S. Pat. No. 7,904,147 entitled SUBSTANTIALLY PLANAR ARTICLE AND METHODS OF MANUFACTURE issued Mar. 8, 2011, which is incorporated by reference herein in its entirety.

In various embodiments the difference of the standard potentials of the first and second reservoirs can be in a range from 0.05 V to approximately 5.0 V. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment the difference of the standard potentials of the first and second reservoirs can be at least 0.05 V, or at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials. Further disclosure relating to standard potentials can be found in U.S. Pat. No. 8,224,439 entitled BATTERIES AND METHODS OF MANUFACTURE AND USE issued Jul. 17, 2012, which is incorporated be reference herein in its entirety.

The voltage present at the site of surgical pre-treatment is typically in the range of millivolts but disclosed embodiments can introduce a much higher voltage, for example near 1 volt when using the 1 mm spacing of dissimilar metals already described. The higher voltage is believed to drive the current deeper into the treatment area. In this way the current not only can drive silver and zinc into the treatment if desired for treatment, but the current can also provide a stimulatory current so that the entire surface area can be treated. The higher voltage may also increase antimicrobial effect bacteria and preventing biofilms. The electric field can also have beneficial effects on cell migration, ATP production, and angiogenesis.

Embodiments disclosed herein relating to surgical pre-treatment can also comprise selecting a patient or tissue in need of, or that could benefit by, surgical pre-treatment.

While various embodiments have been shown and described, it will be realized that alterations and modifications can be made thereto without departing from the scope of the following claims. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then be applied to a surface to create voltaic cells which will become active when brought into contact with an electrolytic solution.

Certain embodiments include LLEC or LLEF systems comprising embodiments designed to be used on irregular, non-planar, or "stretching" surfaces. Embodiments disclosed herein can be used with numerous irregular surfaces of the body, including the face, the shoulder, the elbow, the wrist, the finger joints, the hip, the knee, the ankle, the toe joints, etc. Additional embodiments disclosed herein can be used in areas where tissue is prone to movement, for example the eyelid, the ear, the lips, the nose, the shoulders, the back, etc.

Figure 9:
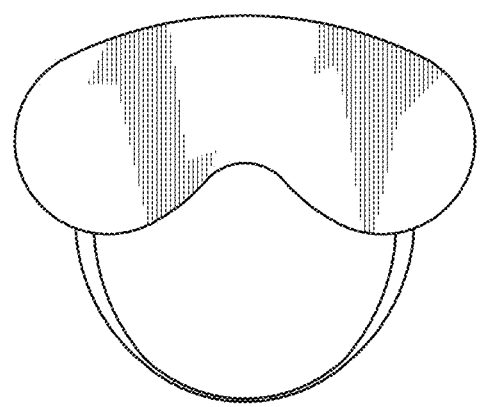
FIG. 9 depicts an embodiment showing a mask comprising a multi-array matrix of biocompatible microcells and means for securing the mask.

In certain embodiments, the substrate can be shaped to fit a particular region of the body. As shown in FIG. 9, a mask-shaped substrate 94 can be used for the surgical pre-treatment around the face and forehead. Embodiments can also include means for securing the mask 94 to the user's head 36. In an embodiment the portion of the mask or substrate that is to contact the skin comprises a multi-array matrix of biocompatible microcells. In certain embodiments a fluid or cream such as a conductive antibacterial fluid or cream can be applied between the multi-array matrix of biocompatible microcells and the skin.

Figure 10:
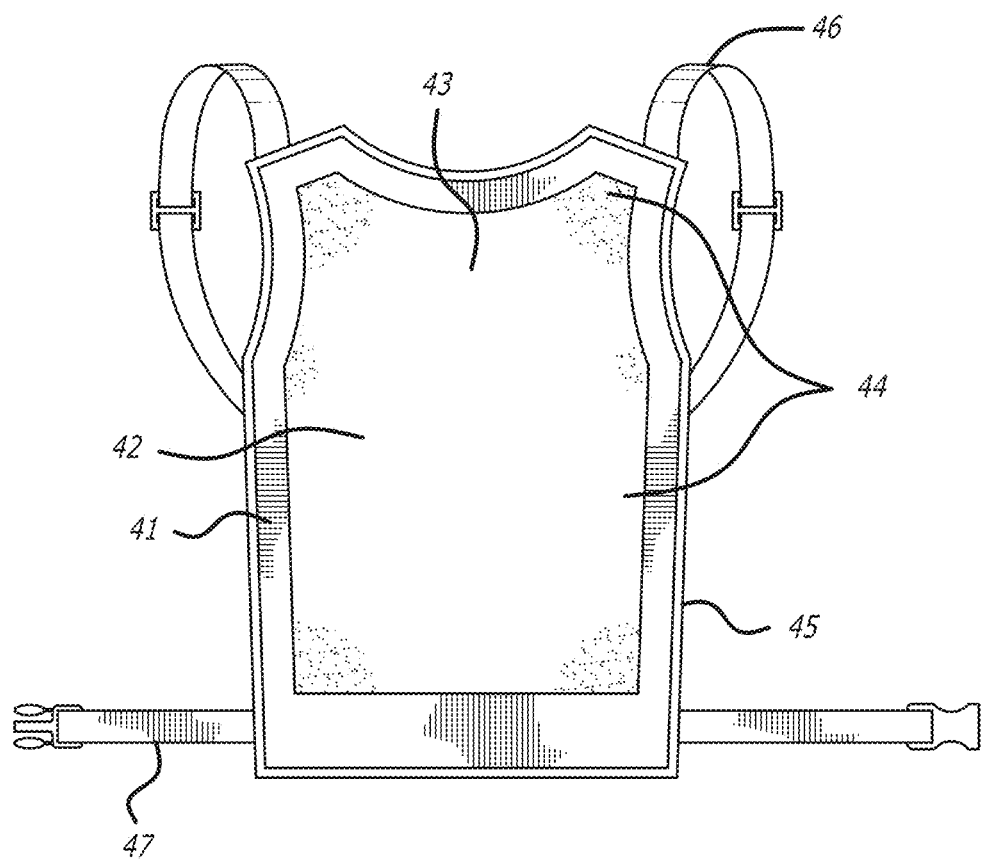
FIG. 10 depicts an embodiment for pre-treating prior to surgery on the back.

Similarly, FIG. 10 depicts an embodiment designed to treat the back prior to surgery. Water impermeable barrier 41 prevents or minimizes liquid from escaping from the device. Hydration material 42 is between 41 and a multi-array matrix of biocompatible microcells layer 43. The hydration material 42 moistens layer 43. Adhesive velcro (or other suitable adhesion device) areas 44 affix layers 42 and 43 to layer 41. Edging material 45 is soft and flexible and protects the user from discomfort. Shoulder straps 46 are made of a soft, flexible material and ensure a secure fit on the patient. Soft, flexible waist strap 47 secures the lower portion of the embodiment to the patient.

Various apparatus embodiments which can be referred to as "medical batteries" are described herein. Further disclosure relating to this technology can be found in U.S. Pat. No. 7,672,719 entitled BATTERIES AND METHODS OF MANUFACTURE AND USE issued Mar. 2, 2010, which is incorporated herein by reference in its entirety.

Certain embodiments disclosed herein include a method of manufacturing a substantially planar LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises joining using tattooing. In embodiments the substrate can comprise gauzes comprising dots or electrodes.

Further embodiments can include a method of manufacturing a LLEC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises: combining the multiple first reservoirs, the multiple second reservoirs, and multiple parallel insulators to produce a pattern repeat arranged in a first direction across a plane, the pattern repeat including a sequence of a first one of the parallel insulators, one of the multiple first reservoirs, a second one of the parallel insulators, and one of the multiple second reservoirs; and weaving multiple transverse insulators through the first parallel insulator, the one first reservoir, the second parallel insulator, and the one second reservoir in a second direction across the plane to produce a woven apparatus.

Embodiments disclosed herein include LLEC and LLEF systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be rejuvenated. Further disclosure relating to materials that can produce an electrical stimulus can be found in U.S. Pat. No. 7,662,176 entitled FOOTWEAR APPARATUS AND METHODS OF MANUFACTURE AND USE issued Feb. 16, 2010, which is incorporated herein by reference in its entirety.

In embodiments "ink" or "paint" can comprise any conductive solution suitable for forming an electrode on a surface, such as a conductive metal solution. In embodiments "printing" or "painted" can comprise any method of applying a conductive material such as a conductive liquid material to a material upon which a matrix is desired, such as a fabric.

In embodiments printing devices can be used to produce LLEC or LLEF systems disclosed herein. For example, inkjet or "3D" printers can be used to produce embodiments.

In certain embodiments the binders or inks used to produce LLEC or LLEF systems disclosed herein can include, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicon, can be added to enhance scar reduction. Such materials can also be added to the spaces between reservoirs.

In embodiments, fabric embodiments disclosed herein can be woven of at least two types of fibers; fibers comprising sections treated or coated with a substance capable of forming a positive electrode; and fibers comprising sections treated or coated with a substance capable of forming a negative electrode. The fabric can further comprise fibers that do not form an electrode. Long lengths of fibers can be woven together to form fabrics. For example, the fibers can be woven together to form a regular pattern of positive and negative electrodes.

Embodiments disclosed herein include a multilayer fabric, for example a layer that can produce an LLEC/LLEF as described herein, a hydration layer, and a waterproof layer.

LLEC/LLEF Systems, Devices, and Methods of Use

In embodiments, methods and devices disclosed herein can be used for to pre-treat areas where surgery is to be performed. Methods disclosed herein can include applying a disclosed embodiment to an area to be treated. Embodiments can include selecting or identifying a patient in need of treatment. In embodiments, methods disclosed herein can include application of an antibacterial agent to an area to be treated. In certain embodiments, disclosed methods include application of an antibacterial to a device disclosed herein.

In embodiments, disclosed methods include application to the treatment area or the device of an antibacterial. In embodiments the antibacterial can be, for example, alcohols, aldehydes, halogen-releasing compounds, peroxides, anilides, biguanides, bisphenols, halophenols, heavy metals, phenols and cresols, quaternary ammonium compounds, and the like. In embodiments the antibacterial agent can comprise, for example, ethanol, isopropanol, glutaraldehyde, formaldehyde, chlorine compounds, iodine compounds, hydrogen peroxide, ozone, peracetic acid, formaldehyde, ethylene oxide, triclocarban, chlorhexidine, alexidine, polymeric biguanides, triclosan, hexachlorophene, PCMX (p-chloro-m-xylenol), silver compounds, mercury compounds, phenol, cresol, cetrimide, benzalkonium chloride, cetylpyridinium chloride, ceftolozane/tazobactam, ceftazidime/avibactam, ceftaroline/avibactam, imipenem/MK-7655, plazomicin, eravacycline, brilacidin, and the like.

In embodiments, disclosed methods include application to the treatment area of a cosmetic agent. Examples of suitable cosmetic agents include, but are not limited to: inorganic sunscreens such as titanium dioxide and zinc oxide; organic sunscreens such as octyl-methoxy cinnamates; retinoids; dimethylaminoathanol (DMAE), copper containing peptides, vitamins such as vitamin E, vitamin A, vitamin C, and vitamin B and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; tetrahydroxypropyl ethylene-diamine, N,N,N',N'-Tetrakis(2-hydroxypropyl)ethylenediamine (THPED); and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts and prodrugs thereof In embodiments, the cosmetic agent contains a depigmentation agent. Examples of suitable depigmentation agents include, but are not limited to: soy extract; soy isoflavones;

retinoids such as retinol; kojic acid; kojic dipalmitate; hydroquinone; arbutin; transexamic acid; vitamins such as niacin and vitamin C; azelaic acid; linolenic acid and linoleic acid; placertia; licorice; and extracts such as chamomile and green tea; and salts and prodrugs and combinations thereof.

In embodiments, compounds that modify resistance to common antibacterials can be employed. For example, some resistance-modifying agents may inhibit multidrug resistance mechanisms, such as drug efflux from the cell, thus increasing the susceptibility of bacteria to an antibacterial. In embodiments, these compounds can include Phe-Arg-β-naphthylamide, or β-lactamase inhibitors such as clavulanic acid and sulbactam.

In an exemplary embodiment, a method disclosed herein comprises applying a conductive antibacterial to an area where treatment is desired, then applying over the agent a bioelectric device that comprises a multi-array matrix of biocompatible microcells.

Certain embodiments include LLEC or LLEF systems comprising embodiments designed to be used on irregular, non-planar, or "stretching" surfaces. Embodiments disclosed herein can be used with numerous irregular surfaces of the mouth, including the gingiva, hard palate, soft palate, molars, premolars, canine, incisors, frenulum of upper lip, frenulum of lower lip, superior vestibule, inferior vestibule, tongue, fauces, etc. Additional embodiments disclosed herein can be used in areas where tissue is prone to movement, for example the inner cheek, upper and lower lip, etc.

In certain embodiments, the substrate can be shaped to fit a particular region of the oral cavity. Embodiments include methods and devices for treating oral diseases in a patient in the need thereof. This method can comprise a oral cavity device for example a mouth guard, a mouth tray, a dental retainer, dental bridges, dentures, or the like with a LLEC and LLEF system attached, printed, connected, etched, implanted or the like on the surface or subsurface.

In an embodiment, methods and devices disclosed herein can be used to treat oral conditions in a patient in need thereof. Examples of such treatments include the treatment of stomatitis (e.g., canker sores, and cold sores); periodontitis (e.g., aggressive periodontitis, chronic periodontitis, peridontitis as a manifestation of systemic disease, or necrotizing periodontal disease); gingivitis (e.g., acute gingivitis, or chronic gingivitis); tooth decay (e.g., smooth surface, or pit and fissure, or root); apthous ulcer (e.g., minor ulcers, or major ulcers, or herpetiform ulcers); systemic lupus erythematosus; and bleeding disorders.

In embodiments, methods and devices disclosed herein can be used after an oral surgery on a patient in the need thereof, for example, endodontic surgery (e.g., root canal, or pulpotomy, or pulpectomy, or apicoectomy); prosthodontics (e.g., implants, or veneers, or bridges, or dentures, or implant-supported prosthesis); orthodontic treatment (e.g., implants and implant-supported prosthesis, or extraction, or fiberotomy); periodontics treatment (e.g., gum recession, or gum graft, or dental implant, or scaling and root planing, or chronic periodontitis); oral and maxillofacial procedure (e.g., dentoalveolar, osseointegrated dental implants, or cheek augmentation, or lip enhancement); cleft pallet procedures (e.g., cleft lip repair, or repair soft palate, or repair hard palate, or bone grafting of the jaw, or any further oral corrections).

Embodiments disclosed herein can comprise a method for killing bacteria and then repairing damaged tissue for a patient in the need thereof. For example, embodiments can comprise a gauze pad, absorbent beads, mouth guard, mouth tray, or the like that can be pressed up or be in contact with the gums, teeth, or other parts of the oral cavity. In embodiments disclosed herein the bacteria can be for example, *Staphylococcus epidermidis, Staphylococcus aureus, Streptococcus mitis, Streptococcus salivarius, Streptococcus mutans, Enterococcus faecalis, Bacteroides* sp., *Lactobacillus* sp., fungus, yeast, viruses, or the like.

Embodiments disclosed herein can comprise dental products. For example, embodiments can comprise a gum or tooth cream wherein the gum or tooth cream is applied on the gums or on and between the teeth and the electrode surface. Embodiments disclosed herein can comprise an oral procedure. For example, embodiments can be employed before, after, or during an oral procedure, such as before, after, or during a gum graft, tooth cleaning, or tooth extraction. Certain embodiments can comprise use of a device disclosed herein before, after, or during a resurfacing procedure.

In embodiments, the oral product disclosed herein can comprise an anti-plaque active agent and anti-tartar agent. Examples of anti-plaque and anti-tartar agents include, but are not limited to fluoride, xylitol, triclosan/copolymer, stannous fluoride, triclosan/copolymer, pyropohosphate, hexametaphosphate, zinc, chlorine dioxide, zinc chloride, potassium nitrate, potassium citrate, potassium chloride, stannous fluoride, strontium chloride, calcium carbonate, silicas, magnesium carbonate, aluminum oxide, and argonite.

Figure 15:
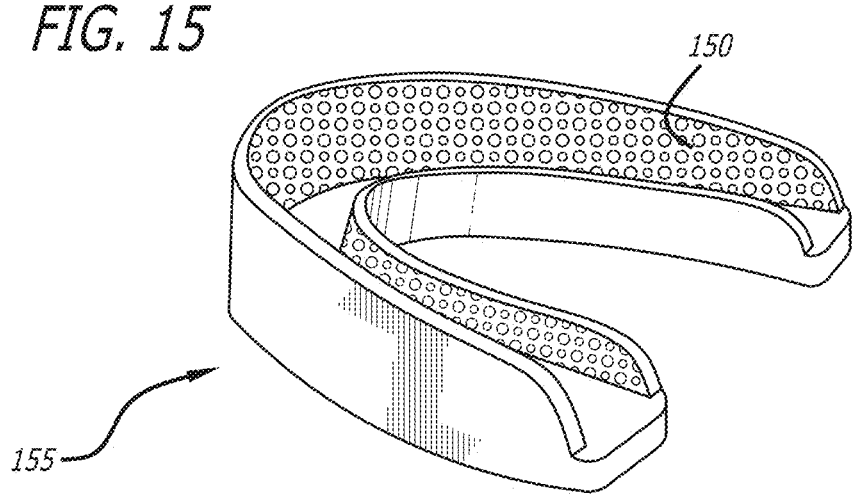
FIG. 15 depicts an embodiment as disclosed for oral use.

In an exemplary embodiment, a method disclosed herein comprises applying a conductive oral product to an area where treatment is desired, then applying over the oral product a bioelectric device that comprises a multi-array matrix of biocompatible microcells. An embodiment as disclosed can comprise the dental tray shown in FIG. 15. Device interior 150 comprises a multi-array matrix of biocompatible microcells. Such matrices can include a first array comprising a pattern of microcells, for example formed from a first conductive solution, the solution including a metal species; and a second array comprising a pattern of microcells, for example formed from a second conductive solution, the solution including a metal species capable of defining at least one voltaic cell for spontaneously generating at least one electrical current with the metal species of the first array when said first and second arrays are introduced to an electrolytic solution and said first and second arrays are not in physical contact with each other. Device exterior 155 can comprise a smooth surface to maximize user comfort. In embodiments, the device comprises discontinuous regions.

Embodiments disclosed herein comprise catheters and catheter dressings comprising a multi-array matrix of biocompatible microcells. Such matrices can include a first array comprising a pattern of microcells, for example formed from a first conductive solution, the solution including a metal species; and a second array comprising a pattern of microcells, for example formed from a second conductive solution, the solution including a metal species capable of defining at least one voltaic cell for spontaneously generating at least one electrical current with the metal species of the first array when said first and second arrays are introduced to an electrolytic solution and said first and second arrays are not in physical contact with each other.

Figure 16:
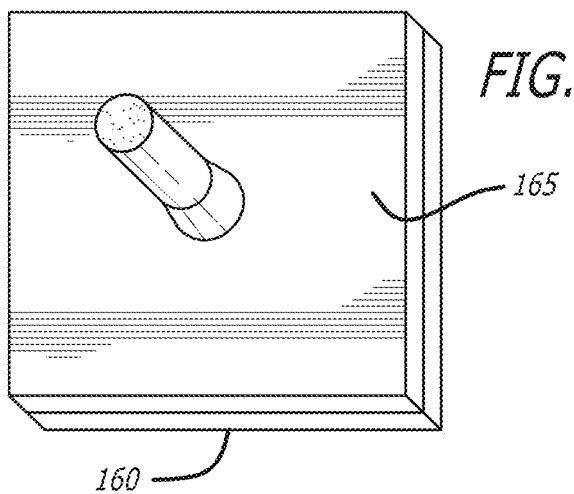
FIG. 16 depicts a catheter dressing as disclosed herein.

As depicted in FIG. 16, a catheter dressing can include a layer 165 formed to shape around a catheter. The layer can comprise any suitable material, for example a thermoformable polymer. The catheter dressing further comprises one or more layers comprising the multi-array matrix of biocompatible microcells 160. In embodiments, the dressing is held in place with an additional bandage, for example a Tegaderm 1626W. In embodiments the various layers are joined, for example with an adhesive. In embodiments, the one or more layers comprising the biocompatible microcells comprise an adhesive. In embodiments, the one or more layers comprising the biocompatible microcells are clear or transparent.

Figure 17:
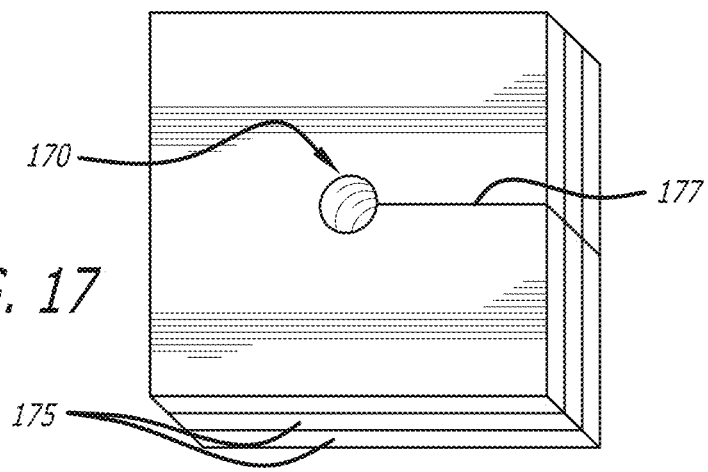
FIG. 17 depicts a catheter dressing as disclosed herein.

FIG. 17 shows an additional embodiment comprising a catheter insertion or puncture site 170, as well as a "slit" 177 in the dressing to aid in dressing application and removal. The catheter dressing further comprises one or more layers comprising the multi-array matrix of biocompatible microcells 175. In embodiments, the dressing is held in place with an additional bandage, for example a Tegaderm 1626W.

In embodiments, the one or more layers comprising the multi-array matrix of biocompatible microcells can be, for example, less than 1 mm thick, 1 mm thick, more than 1 mm thick, more than 2 mm thick, more than 3 mm thick, more than 4 mm thick, more than 5 mm thick, more than 6 mm thick, more than 7 mm thick, more than 8 mm thick, more than 9 mm thick, more than 10 mm thick, more than 15 mm thick, more than 20 mm thick, more than 30 mm thick, more than 40 mm thick, more than 50 mm thick, or the like.

In embodiments, catheter dressings disclosed herein can be used for any suitable clinical application. For example, the disclosed catheter dressings can be used for IV sites, PICC lines, Hickman catheter sites, and the like.

EXAMPLES

The following non-limiting examples are provided for illustrative purposes only in order to facilitate a more complete understanding of representative embodiments. These examples should not be construed to limit any of the embodiments described in the present specification.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch.

Human keratinocytes were plated under plated under placebo or a LLEC system described herein (labeled "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1 R phosphorylation was demonstrated by the cells plated under the PROCELLERA® device as compared to cells plated under insulin growth factor alone.

Integrin accumulation also affects cell migration. An increase in integrin accumulation was achieved with the LLEC system. Integrin is necessary for cell migration, and is found on the leading edge of migrating cell.

Thus, the tested LLEC system enhanced cellular migration and IGF-1 R/integrin involvement. This involvement demonstrates the effect that the LLEC system had upon cell receptors involved with the wound healing process.

Example 2

Wound Care Study

The medical histories of patients who received "standard-of-care" wound treatment ("SOC"; n=20), or treatment with a LLEC device as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLEC received one application of the device each week, or more frequently in the presence of excessive wound exudate, in conjunction with appropriate wound care management. The LLEC was kept moist by saturating with normal saline or conductive hydrogel. Adjunctive therapies (such as negative pressure wound therapy [NPWT], etc.) were administered with SOC or with the use of LLEC unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLEC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLEC group). Additionally, the patients often had multiple co-morbidities, including diabetes, renal disease, and hypertension. The average number of days to wound closure was 36.25 (SD=28.89) for the SOC group and 19.78 (SD=14.45) for the LLEC group, p=0.036. On average, the wounds in the LLEC treatment group attained closure 45.43% earlier than those in the SOC group.

Based on the volume calculated, some wounds improved persistently while others first increased in size before improving. The SOC and the LLEC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLEC group (p=0.018). Overall, wounds in both groups responded positively. Response to treatment was observed to be slower during the initial phase, but was observed to improve as time progressed.

The LLEC wound treatment group demonstrated on average a 45.4% faster closure rate as compared to the SOC group. Wounds receiving SOC were more likely to follow a "waxing-and-waning" progression in wound closure compared to wounds in the LLEC treatment group.

Compared to localized SOC treatments for wounds, the LLEC (1) reduces wound closure time, (2) has a steeper wound closure trajectory, and (3) has a more robust wound healing trend with fewer incidence of increased wound dimensions during the course of healing.

Example 3

LLEC Influence on Human Keratinocyte Migration

An LLEC-generated electrical field was mapped, leading to the observation that LLEC generates hydrogen peroxide, known to drive redox signaling. LLEC-induced phosphorylation of redox-sensitive IGF-1 R was directly implicated in cell migration. The LLEC also increased keratinocyte mitochondrial membrane potential.

The LLEC was made of polyester printed with dissimilar elemental metals. It comprises alternating circular regions of silver and zinc dots, along with a proprietary, biocompatible binder added to lock the electrodes to the surface of a flexible substrate in a pattern of discrete reservoirs. When the LLEC contacts an aqueous solution, the silver positive electrode (cathode) is reduced while the zinc negative electrode (anode) is oxidized. The LLEC used herein consisted of metals placed in proximity of about 1 mm to each other thus forming a redox couple and generating an ideal potential on the order of 1 Volt. The calculated values of the electric field from the LLEC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLEC is in contact with de-ionized water yielded a value of about 0.2 Volts. Though the potential difference between zinc and silver dots can be measured, non-intrusive measurement of the electric field arising from contact between the LLEC and liquid medium was difficult. Keratinocyte migration was accelerated by exposure to an Ag/Zn LLEC. Replacing the Ag/Zn redox couple with Ag or Zn alone did not reproduce the effect of keratinocyte acceleration.

Exposing keratinocytes to an LLEC for 24 h significantly increased green fluorescence in the dichlorofluorescein (DCF) assay indicating generation of reactive oxygen species under the effect of the LLEC. To determine whether $H_2O_2$ is generated specifically, keratinocytes were cultured with a LLEC or placebo for 24 h and then loaded with PF6-AM (Peroxyfluor-6 acetoxymethyl ester; an indicator of endogenous $H_2O_2$). Greater intracellular fluorescence was observed in the LLEC keratinocytes compared to the cells grown with placebo. Over-expression of catalase (an enzyme that breaks down $H_2O_2$) attenuated the increased migration triggered by the LLEC. Treating keratinocytes with N-Acetyl Cysteine (which blocks oxidant-induced signaling) also failed to reproduce the increased migration observed with LLEC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential (Am). Fluorescent dyes JC-1 and TMRM were used to measure mitochondrial membrane potential. JC-1 is a lipophilic dye which produces a red fluorescence with high Am and green fluorescence when Am is low. TMRM produces a red fluorescence proportional to Am. Treatment of keratinocytes with LLEC for 24 h demonstrated significantly high red fluorescence with both JC-1 and TMRM, indicating an increase in mitochondrial membrane potential and energized mitochondria under the effect of the LLEC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLEC was examined next. More than two fold enhancement of basal glucose uptake was observed after treatment with LLEC for 24 h as compared to placebo control.

Keratinocyte migration is known to involve phosphorylation of a number of receptor tyrosine kinases (RTKs). To determine which RTKs are activated as a result of LLEC, scratch assay was performed on keratinocytes treated with LLEC or placebo for 24 h. Samples were collected after 3 h and an antibody array that allows simultaneous assessment of the phosphorylation status of 42 RTKs was used to quantify RTK phosphorylation. It was determined that LLEC significantly induces IGF-1 R phosphorylation. Sandwich ELISA using an antibody against phospho-IGF-1 R and total IGF-1 R verified this determination. As observed with the RTK array screening, potent induction in phosphorylation of IGF-1 R was observed 3 h post scratch under the influence of LLEC. IGF-1 R inhibitor attenuated the increased keratinocyte migration observed with LLEC treatment.

MBB (monobromobimane) alkylates thiol groups, displacing the bromine and adding a fluoresce nt tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLEC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLEC-driven cell migration is prevented. The observation that the LLEC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit alpha-v. There is evidence that integrin, a major extracellular matrix receptor, polarizes in response to applied ES and thus controls directional cell migration. It may be noted that there are a number of integrin subunits, however we chose integrin av because of evidence of association of alpha-v integrin with IGF-1 R, modulation of IGF-1 receptor signaling, and of driving keratinocyte locomotion. Additionally, integrin alpha v has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLEC-induced IGF-1 R mediated keratinocyte migration are a5 integrin and a6 integrin.

Materials and Methods

Cell culture—Immortalized HaCaT human keratinocytes were grown in Dulbecco's low-glucose modified Eagle's medium (Life Technologies, Gaithersburg, Md., U.S.A.) supplemented with 10% fetal bovine serum, 100 U/ml penicillin, and 100 µg/ml streptomycin. The cells were maintained in a standard culture incubator with humidified air containing 5% $CO_2$ at 37° C.

Scratch assay—A cell migration assay was performed using culture inserts (IBIDI®, Verona, Wis.) according to the manufacturers instructions. Cell migration was measured using time-lapse phase-contrast microscopy following withdrawal of the insert. Images were analyzed using the AxioVision Rel 4.8 software.

N-Acetyl Cysteine Treatment—Cells were pretreated with 5 mM of the thiol antioxidant N-acetylcysteine (Sigma) for 1 h before start of the scratch assay.

IGF-1 R inhibition—When applicable, cells were preincubated with 50 nM IGF-1 R inhibitor, picropodophyllin (Calbiochem, MA) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with 2.3×107 pfu AdCatalase or with the empty vector as control in 750 µl of media. Subsequently, 750 µl of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1 R were measured using a DuoSet IC ELISA kit from R&D Systems.

Determination of Mitochondrial Membrane Potential—Mitochondrial membrane potential was measured in HaCaT cells exposed to the LLEC or placebo using TMRM or JC-1 (MitoProbe JC-1 Assay Kit for Flow Cytometry, Life Technologies), per manufacturers instructions for flow cytometry.

Integrin alpha V Expression—Human HaCaT cells were grown under the MCD or placebo and harvested 6 h after removing the IBIDI® insert. Staining was done using antibody against integrin aV (Abcam, Cambridge, Mass.).

Example 4

Induction of Pre-Angiogenic Responses in Vascular Endothelial Cells by Signaling Through VEGF Receptors Materials and Methods Cell Cultures and Reagents Tissue culture reagents were obtained from Life Technologies UK. The VEGFR inhibitor (catalog number 676475), the PI3K inhibitor LY294002 (catalog number 440202), the Akt inhibitor (catalog number 124005) and the Rho kinase inhibitor Y27632 (catalog number 688001) were all obtained from Calbiochem. Rhodamine-phalloidin (E3478) was obtained from Molecular Probes (Leiden, The Netherlands) and anti-tubulin conjugated with FITC was obtained from Sigma. The HUVEC cell line from ATCC was used prior to passage 10. Dulbecco's modified Eagle's medium (DMEM) with 10% fetal bovine serum (FBS) was used for culture cells and EF exposure experiments.

Electric Field (EF) Stimulation

HUVEC cells were seeded in a trough formed by two parallel (1 cm apart) strips of glass coverslip (No. 1, length of 22 mm) fixed to the base of the dish with silicone grease. Scratch lines were made perpendicular to the long axis of the chamber with a fine sterile needle and used as reference marks for directed cell migration. Cells were incubated for 24-48 hours (37° C., 5% $CO_2$) before a roof coverslip was applied and sealed with silicone grease. The final dimensions of the chamber, through which current was passed, were 22×10×0.2 mm. Agar-salt bridges not less than 15 cm long were used to connect silver/silver-chloride electrodes in beakers of Steinberg's solution (58 mM NaCl, 0.67 mM KCl, 0.44 mM $Ca(NO_3)_2$, 1.3 mM $MgSO_4$, 4.6 mM Trizma base, pH 7.8-8.0), to pools of excess culture medium at either side of the chamber. Field strengths were measured directly at the beginning of, the end of and during each experiment. No fluctuations in field strength were observed. For drug inhibition experiments, cells were incubated with the VEGFR inhibitor 4-[(4'-chloro-2'-fluoro)phenylamino]-6,7-dimethoxyquinazoline (50 µM), the PI3K inhibitor LY294002 (50 µM), an Akt inhibitor 1-L-6-hydroxymethyl-chiro-inositol 2-[(R)-2-O-methyl-3-O-octadecylcarbonate] (50 µM), the Rho kinase inhibitor Y27632 (50 µM), both Akt and Rho kinase inhibitors (10 µM each) or latrunculin (50 nM) for 1 hour before EF stimulation. The same concentration of drug was present during EF exposure in a $CO_2$ incubator.

Quantification of Cell Behavior

A series of images was taken with an image analyser immediately before EF exposure and at 4, 8 and 24 hours of EF exposure. Cell orientation was quantified as an orientation index (Oi), which is defined as Oi=cos 2($\alpha$), where $\alpha$ is the angle formed by the long axis of a cell with a line drawn perpendicular to the field lines. A cell with its long axis parallel to the vector of the EF will have an Oi of −1, and a cell with its long axis exactly perpendicular to the EF vector will have an Oi of +1. A randomly oriented population of cells will have an average Oi {defined as [$\Sigma_n$ cos 2($\alpha$)]÷n} of 0. The significance of this two-dimensional orientation distribution against randomness was calculated using Rayleigh's distribution. A long:short axis ratio was calculated for assessment of elongation.

Mean migration rate and directedness were quantified over 4 hours because cells multiplied during longer EF exposures, making it difficult to define a clear migration path. The angle (θ) that each cell moved with respect to the imposed EF vector was measured. The cos(θ) (directedness) is +1, if the cell moved directly along the field lines toward the cathode, 0 if the cell moved perpendicular to the EF vector and −1 if the cell moved directly towards the positive pole. Averaging the cosines $\{[\Sigma_i \cos(\theta)] \div N$, where N is the total number of cells$\}$ yields an average directedness of cell movement.

A commercially available VEGF165 ELISA kit was obtained from R and D (Minneapolis, Minn.), and the detailed technical instructions were followed. Confocal microscopy was as described. Statistical analyses were performed using unpaired, two-tailed Student's t-test. Data are expressed as mean±s.e.m.

Results

Cells cultured without exposure to the EF had the typical cobblestone morphology, with the long axis of the cell body oriented randomly. In contrast, endothelial cells cultured in DC EFs underwent a reorientation, with their long axis coming to lie perpendicular to the vector of the applied EF. This elongation and alignment in an applied EF resembles the response of endothelial cells to fluid shear stress.

Cell alignment was quantified using an orientation index Oi=cos 2(α), where α is the angle formed between the long axis of a cell and a line drawn perpendicular to the field lines. In cells oriented perpendicular to the field vector, the Oi is +1, cells parallel to the field vector give an Oi of −1 and random orientation gives an Oi of 0. We compared the elongation and reorientation of single cells with those of cells in monolayers. They were broadly similar, with single cells responding quicker and showing a significantly higher Oi (0.56±0.04, n=245) at 4 hours of EF exposure than cells in a monolayer sheet (0.35±0.03, n=528). Both single cells and cells in monolayers, however, had a similar Oi by 8 hours (0.71±0.03, n=227 and 0.62±0.03, n=312, respectively).

The perpendicular orientation of endothelial cells showed both time and voltage dependency. Significant orientation was observed as early as 4 hours after the onset of the EF. A steady increase of Oi indicates gradually increasing perpendicular orientation with continued exposure. Longer EF exposure, up to 3 days at 100 mV mm$^{-1}$ (1 mV across a cell 10 µm wide), induced striking orientation and elongation. EF exposure did not induce any detrimental effects on the cells, which were perfectly healthy for up to 3-4 days in EFs.

Voltage dependency was more obvious at later times, with a higher Oi for cells cultured at higher voltages. After 24 hours at 300 mV mm$^{-1}$, almost all the cells were perpendicular. An EF strength as low as 75 mV mm$^{-1}$ induced significant perpendicular orientation, with Oi of 0.19 (significantly different from random orientation, $p=4.4 \times 10^{-6}$, n=433), whereas an EF of 50 mV mm$^{-1}$ did not. The threshold field strength inducing perpendicular orientation of the endothelial cells was therefore between 50 mV mm$^{-1}$ and 75 mV mm$^{-1}$. This is low, representing only 0.5-0.75 mV across a cell with a diameter of 10 µm.

Reorientation of Endothelial Cells in EFs Requires VEGFR Activation

VEGF activation is a pivotal elements in angiogenic responses and enhanced angiogenesis by electric stimulation in vivo is mediated through VEGFR activation. To test whether EF-induced endothelial cell orientation might involve VEGF signaling, we quantified levels of VEGF. EF exposure (200 mV mm$^{-1}$, the same as that measured at skin wounds) significantly enhanced levels of VEGF released into the culture medium. Marked elevation of VEGF in the culture medium was observed as early as 5 minutes after onset of the EF; this was reduced at 1 hour and 2 hours, rose again at 4 hours, and reached a high level by 24 hours.

Inhibition of VEGFR activation by inhibiting both VEGFR-1 and VEGFR-2 with the drug 4-[(4'-chloro-2'-fluoro)phenylamino]-6,7-dimethoxyquinazoline completely abolished the reorientation of cells in an EF. This drug is a potent VEGFR inhibitor that inhibits the receptor tyrosine kinase activity (50% inhibitory concentrations of 2.0 µM and 100 nM for VEGFR-1 and VEGFR-2, respectively). It is very selective for VEGFR-1 and VEGFR-2 tyrosine kinase activity compared with that associated with the epidermal growth factor (EGF) receptor (50-fold and 3800-fold, respectively). The morphology of the cells treated with VEGFR inhibitor was very similar to control cells. Cells still elongated, although their long axis was slightly reduced, but they were oriented randomly. Inhibition of VEGFRs could conceivably have had detrimental effects on the long-term viability of cells and this could have influenced their orientation responses. To test for this, we compared the orientation response after a short period of inhibitor and EF application. The orientation response was completely abolished at 4 hours and 8 hours in an EF after VEGFR inhibition. The Oi values of the cells treated with VEGFR inhibitor were −0.16±0.05 and −0.05±0.05 in EF for 4 hours and 8 hours, respectively, which is significantly different from the non-inhibitor-treated values of 0.36±0.05 and 0.53±0.05 (P<0.01).

Reorientation of Endothelial Cells Involved the PI3K-Akt Pathway

VEGFR activation lead to endothelial cell migration, cell survival and proliferation, which require the activation of Akt, a downstream effectors of PI3K. Both the PI3K inhibitor LY294002 (50 µM) and the Akt inhibitor (50 µM) significantly decreased the orientation response.

The concentration of either drug alone would be expected to inhibit PI3K and Akt activation completely but neither drug inhibited perpendicular reorientation completely, and significant Oi values remained, indicating that other signaling mechanisms must be involved.

Role of Rho and Integrin in EF-Induced Reorientation of Endothelial Cells

The Rho family of GTPases regulates VEGF-stimulated endothelial cell motility and reorganization of the actin cytoskeleton, which are important in endothelial cell retraction and in the formation of intercellular gaps. The Rho kinase inhibitor, Y27632, decreased the orientation response significantly, with Oi values of 0.55±0.05, 0.45±0.05 and 0.24±0.05 at 10 µM, 20 µM and 50 µM, respectively. Significant Oi values nonetheless remained even at 50 µM, indicating that multiple signaling mechanisms must be involved. Mitogen-activated-protein kinase inhibition with U0126 (50 µM), like Y27632 (0.33±0.03), decreased the orientation to a similar extent.

Because both Akt and Rho kinase inhibitors individually showed partial inhibition, perhaps the two enzymes function in different pathways to induce cell reorientation. To test this, a combination of the two inhibitors was used. The orientation response was abolished completely by using Akt and Rho kinase inhibitors together (both at 10 µM) (Oi=−0.10±0.06; compared to control=0.80±0.09, P<0.0001) (FIG. 3B).

Integrins, especially αvβ3, are important in endothelial cell movement and alignment to shear stress and mechanical stimulation. HUVEC cells were incubated with a blocking antibody against αvβ3 (LM609) (20 µg ml$^{-1}$) for 1 hour and then exposed to an EF (200 mV mm$^{-1}$) with the antibody present. Blocking αvβ3 had no effect on orientation to the EF, cells reoriented normally (Oi=0.72±0.03, n=110, compared with the control=0.80±0.09, n=124, P>0.05).

Small EFs Elongated Endothelial Cells

HUVEC cells elongated dramatically in an EF. By contrast, cells cultured with no EF retained a more-cobblestone-like appearance. Striking cell elongation was induced by a voltage drop of about 0.7-4.0 mV across a cell of ~15 µm in diameter. We quantified the elongation of the cells using a long:short axis ratio. A perfectly round cell has a long:short axis ratio of 1 and, as cells elongate, the ratio increases. Control cells (no EF) showed no increase in long:short axis over 24 hours in culture. Elongation responses were both time and voltage dependent. The long:short axis ratio of EF exposed cells indicated gradual cell elongation throughout the 24 hour experimental period. The voltage dependency of the elongation response was more obvious at later times, with a greater long:short axis ratio for cells cultured at higher EFs. The threshold for EF-induced endothelial cell elongation was between 50-75 mV mm$^{-1}$, again 0.5-0.75 mV across a cell 10 µm in diameter. The elongation response of endothelial cells was more marked than that seen previously at the same EF strengths, in corneal and lens epithelial cells.

VEGFR, PI3K-Akt and Rho Signaling are Involved in the Elongation Response

The signaling elements required for reorientation are also involved in elongation, but there are subtle differences. The VEGFR inhibitor (50 µM) had no effect on the long:short axis ratio of control cells but significantly decreased the long:short axis ratio in EF-treated cells (P<0.002). Both the PI3K inhibitor LY294002 and the Akt inhibitor also significantly decreased the long:short axis ratio (both P<0.0001 versus control). Cells treated with these drugs elongated less, with LY294002 the more effective in suppressing EF-induced elongation. The Rho kinase inhibitor, Y27632 also significantly decreased the long:short axis ratio (P<0.0001, FIG. 5B), whereas the αvβ3-blocking antibody significantly inhibited the elongation response (3.12±0.008 compared with the control 3.65±0.15, P=0.007).

Cytoskeleton Alignment and the Consequence of Actin Filament Disruption

To control changes in cell shape, reorientation and migration, extracellular stimuli initiate intracellular signaling that modifies cytoskeletal organization. Both actin filaments and microtubules were aligned in the direction of cell elongation. Latrunculin A, a toxin inhibiting actin polymerization, completely abolished the EF-induced elongation response and suppressed the orientation response significantly (P<0.001) but not fully.

Small EFs Direct Migration of Endothelial Cells Towards the Anode

Endothelial cells migrated directionally toward the anode when cultured in EFs. The directional migration was slow but steady during the EF exposure and was more evident for single cells than for sheets of cells. Cells migrated directionally towards the anode while elongating and reorienting perpendicularly. Lamellipodial extension toward the anode was marked. Directional migration was obvious at a physiological EF strength of 100 mV mm$^{-1}$. The threshold field strength that could induce directional migration was therefore below 100 mV mm$^{-1}$. Cell migration was quantified as previously and significant anodal migration was evident (P<0.0001). Migration speed, however, remained constant before and after EF exposure, at 1-2 µm hour$^{-1}$, which is significantly slower than most other cell types migrating in an EF.

Example 5

Generation of Superoxide

A LLEC system was tested to determine the effects on superoxide levels which can activate signal pathways. PROCELLERA® LLEC system increased cellular protein sulfhydryl levels. Further, the PROCELLERA® system increased cellular glucose uptake in human keratinocytes. Increased glucose uptake can result in greater mitochondrial activity and thus increased glucose utilization, providing more energy for cellular migration and proliferation. This can "prime" the wound healing process before a surgical incision is made and thus speed incision healing.

Example 6

Effect on *Propionibacterium acnes*

Bacterial Strains and Culture

The main bacterial strain used in this study is *Propionibacterium acnes* and multiple antibiotics-resistant *P. acnes* isolates are to be evaluated.

ATCC medium (7 *Actinomyces* broth) (BD) and/or ATCC medium (593 chopped meat medium) is used for culturing *P. acnes* under an anaerobic condition at 37° C. All experiments are performed under anaerobic conditions.

Culture

LNA (Leeming-Notman agar) medium is prepared and cultured at 34° C. for 14 days.

Planktonic Cells

*P. acnes* is a relatively slow-growing, typically aerotolerant anaerobic, Gram-positive bacterium (rod). *P. acnes* is cultured under anaerobic condition to determine for efficacy of an embodiment disclosed herein (PROCELLERA®). Overnight bacterial cultures are diluted with fresh culture medium supplemented with 0.1% sodium thioglycolate in PBS to 10$^5$ colony forming units (CFUs). Next, the bacterial suspensions (0.5 mL of about 105) are applied directly on PROCELLERA® (2"×2") and control fabrics in Petri-dishes under anaerobic conditions. After 0 h and 24 h post treatments at 37° C., portions of the sample fabrics are placed into anaerobic diluents and vigorously shaken by vortexing for 2 min. The suspensions are diluted serially and plated onto anaerobic plates under an anaerobic condition. After 24 h incubation, the surviving colonies are counted. The LLEC limits bacterial proliferation.

Example 7

Pre-Treatment Prior to Spinal Fusion Surgery

Figure 11:
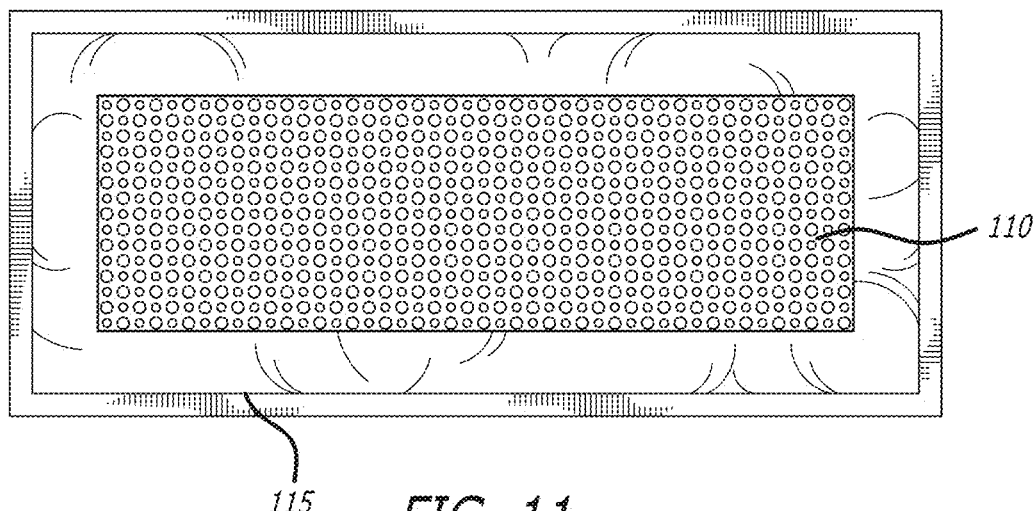
FIG. 11 depicts an embodiment disclosed herein for pre-treatment of a small area. The embodiment includes a hydrated silica pack to maintain hydration of the device.
Figure 12:
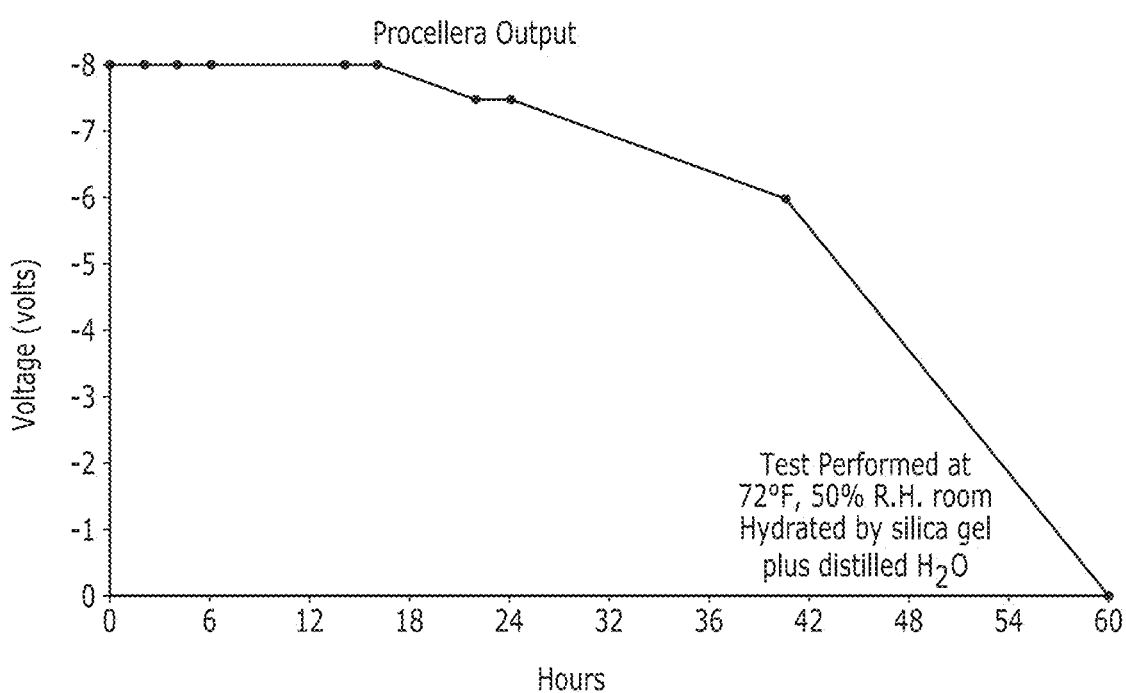
FIG. 12 depicts PROCELLERA® (an embodiment disclosed herein) output over time. The graph shows volts plotted against time in hours.

Prior to spinal fusion surgery, the patient wears a three-layer vest that covers only the back as shown in FIG. 10. The vest consists of a layer of standard PROCELLERA® backed by a hydration layer of polyvinyl alcohol fibers fabricated into a uniform, spongelike open cell pore structure. An outer layer of a waterproof polyester fabric surrounds the hydration layer. A compression shirt is worn over the vest to provide intimate contact between the electrodes and the skin. The vest is soaked in a warm water/salt solution prior to placement on the patient for the night. The material remains hydrated and produces voltage for over 24 hours (see FIGS. 11 and 12). The material is cool to the touch but does not feel wet. A dry shirt can be worn over the vest.

The LLEC initiates the incision-healing process by; 1) reducing or eliminating microorganism presence around the incision site; 2) increasing integrin accumulation; 3) increasing cellular protein sulfhydryl levels; 4) increasing $H_2O_2$ production; and 5) up-regulating the TCA (tricarboxylic acid) cycle.

Example 8

Pre-Treatment Prior to Blepharoplasty

The patient is scheduled to undergo blepharoplasty in 1 week. A mask as seen in FIG. 9 is made with printed electrodes as described herein, using the pattern described in FIG. 1. Prior to donning the mask, the patient applies a conductive agent to the skin around his eyes. The mask and conductive agent are reapplied to the patient's skin each night. After 1 week of nightly wear, the incision-healing process is initiated and accelerated.

Example 9

Pre-Treatment Prior to Brow Lift

The patient is scheduled to undergo a brow lift in 2 week. A mask as seen in FIG. 9 is made with printed electrodes as described herein, using the pattern described in FIG. 1. Prior to donning the mask, the patient applies a conductive agent to the skin around his brow. The mask and conductive agent are reapplied to the patient's skin each night. After 2 weeks of nightly wear, the incision-healing process is initiated and accelerated.

Example 10

Pre-Treatment Prior to Rhinoplasty

The patient is scheduled to undergo rhinoplasty in 1 week. A device with printed electrodes as described herein is shaped to fit over and around the patient's nose. Prior to donning the device, the patient applies a conductive agent to the skin on and around her nose. The mask and conductive agent are reapplied to the patient's skin each night. After 1 week of nightly wear, the incision-healing process is initiated and accelerated.

Example 11

Pre-Treatment Prior to Rotator Cuff Surgery

Figure 8A:
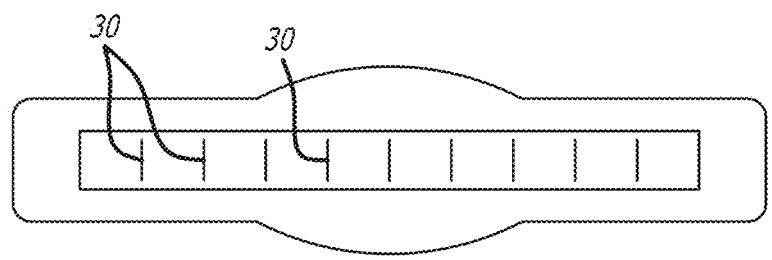
FIG. 8 depicts alternate embodiments showing the location of discontinuous regions as well as anchor regions of the system.
Figure 8B:
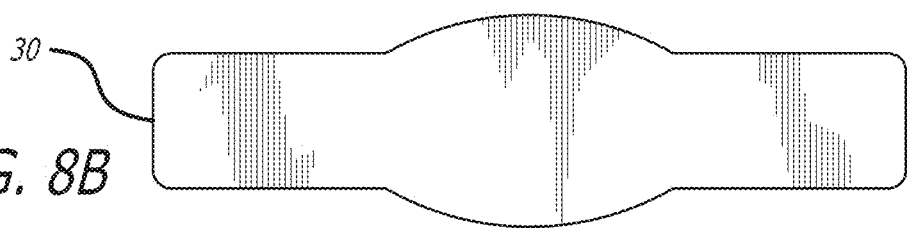
Figure 8C:
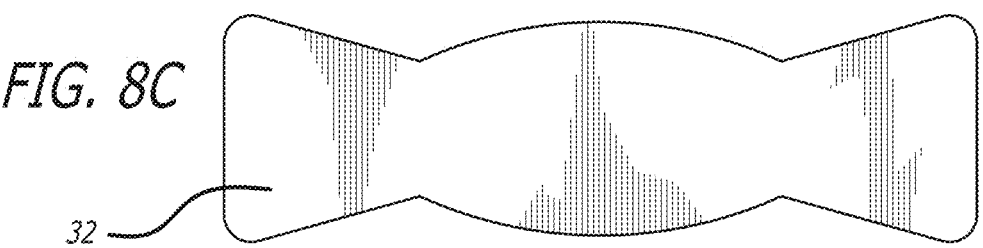
Figure 8D:
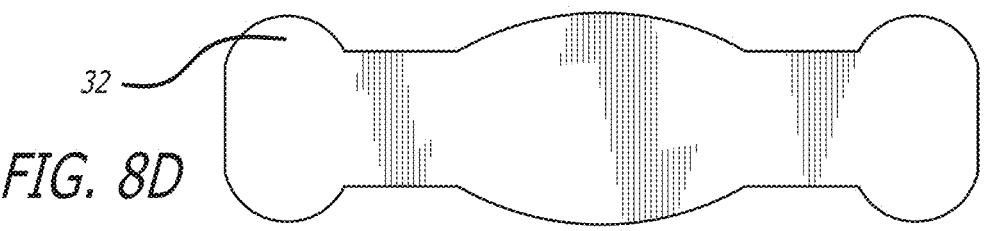
Figure 8E:
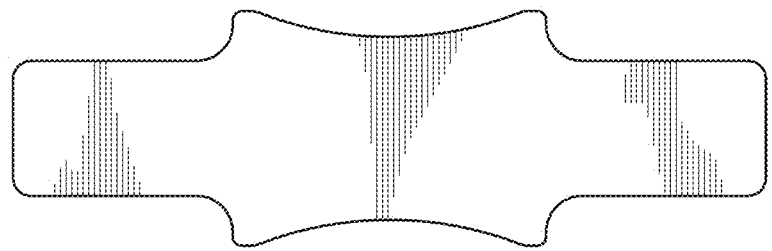

A patient is scheduled to undergo rotator cuff surgery. A device with printed electrodes and void regions (as shown in FIG. 8A) to aid in fitting around the patient's shoulder is prepared. Prior to donning the device, the patient applies a conductive agent to the skin on and around his shoulder. The device and conductive agent are reapplied to the patient's skin each night. After wearing the device for 24 hours prior to the surgery (the conductive agent is reapplied every 6 hours), the incision-healing process is initiated and accelerated.

Example 12

Making an Electroceutical Fabric

An electroceutical fabric is produced by weaving fibers wherein sections of the fibers are coated or treated with materials capable of producing electricity and forming a battery in the presence of an electrolyte.

Figure 13:
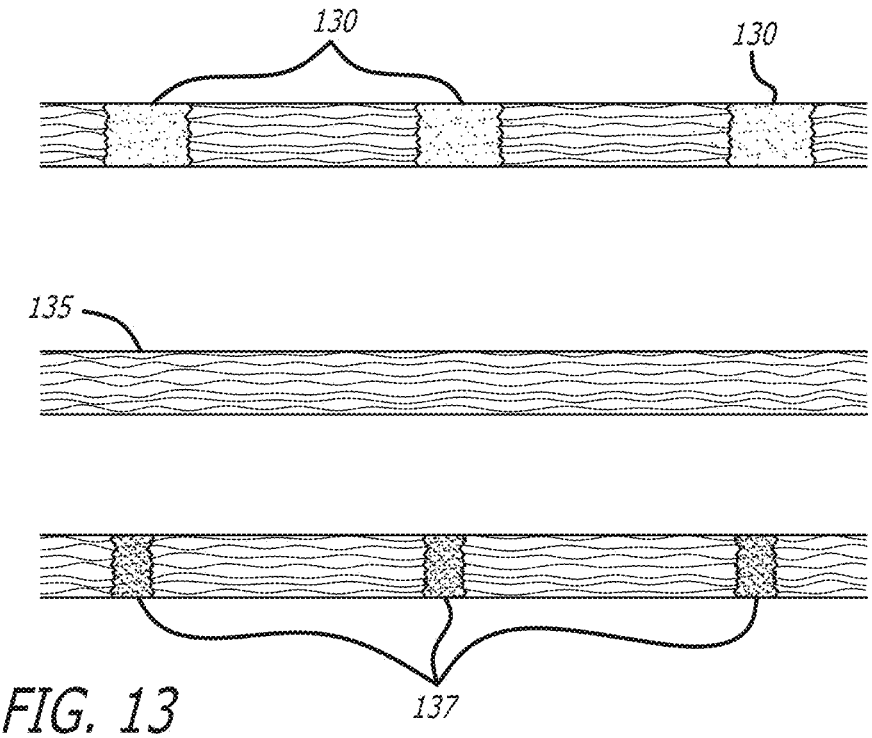
FIG. 13 depicts an electroceutical fabric as described herein.

The fabric is woven of three types of fibers; fibers comprising discrete sections spray coated with silver forming a positive electrode; fibers comprising discrete sections spray coated with zinc forming a negative electrode; and fibers that do not form an electrode. The individual fibers are shown in FIG. 13. Silver deposits 130 form microbatteries with zinc deposits 137 when in common contact with a conductive material.

The fabric is seen in FIG. 14. Silver deposits 140 form microbatteries with zinc deposits 145 when in common contact with a conductive material.

Example 13

Modulation of Bacterial Gene Expression and Enzyme Activity

Treatment of biofilms presents a major challenge, because bacteria living within them enjoy increased protection against host immune responses and are markedly more tolerant to antibiotics. Bacteria residing within biofilms are encapsulated in an extracellular matrix, consisting of several components including polysaccharides, proteins and DNA which acts as a diffusion barrier between embedded bacteria and the environment thus retarding penetration of antibacterial agents. Additionally, due to limited nutrient accessibility, the biofilm-residing bacteria are in a physiological state of low metabolism and dormancy increasing their resistance towards antibiotic agents.

Chronic wounds present an increasing socio-economic problem and an estimated 1-2% of western population suffers from chronic ulcers and approximately 2-4% of the national healthcare budget in developed countries is spent on treatment and complications due to chronic wounds. The incidence of non-healing wounds is expected to rise as a natural consequence of longer lifespan and progressive changes in lifestyle like obesity, diabetes, and cardiovascular disease. Non-healing skin ulcers are often infected by biofilms. Multiple bacterial species reside in chronic wounds; with *Pseudomonas aeruginosa*, especially in larger wounds, being the most common. *P. aeruginosa* is suspected to delay healing of leg ulcers. Also, surgical success with split graft skin transplantation and overall healing rate of chronic venous ulcers is presumably reduced when there is clinical infection by *P. aeruginosa*.

*P. aeruginosa* biofilm is often associated with chronic wound infection. The BED ("BED" or "bioelectric device" or PROCELLERA® as disclosed herein) consists of a matrix of silver-zinc coupled biocompatible microcells, which in the presence of conductive wound exudate activates to generate an electric field (0.3-0.9V). Growth (measured as O.D and cfu) of pathogenic *Pseudomonas aeruginosa* strain PAO1 in LB media was markedly arrested in the presence of the BED (p<0.05, n=4). PAO1 biofilm was developed in vitro using a polycarbonate filter model. Grown overnight in LB medium at 37° C. bacteria were cultured on sterile polycarbonate membrane filters placed on LB agar plates and allowed to form a mature biofilm for 48 h. The biofilm was then exposed to BED or placebo for the following 24 h. Structural characterization using scanning electron microscopy demonstrated that the BED markedly disrupted biofilm integrity as compared to no significant effect observed using a commercial silver dressing commonly used for wound care. Staining of extracellular polymeric substance, PAO1 staining, and a vital stain demonstrated a decrease in biofilm thickness and number of live bacterial cells in the presence of BED (n=4). BED repressed the expression of quorum sensing genes lasR and rhlR ($p<0.05$, n=3). BED was also found to generate micromolar amounts of superoxide (n=3), which are known reductants and repress genes of the redox sensing multidrug efflux system mexAB and mexEF (n=3, $p<0.05$). BED also down-regulated the activity of glycerol-3-phosphate dehydrogenase, an electric field sensitive enzyme responsible for bacterial respiration, glycolysis, and phospholipid biosynthesis ($p<0.05$, n=3).

Materials and Methods

In-Vitro Biofilm Model

PAO1 biofilm was developed in vitro using a polycarbonate filter model. Cells were grown overnight in LB medium at 37° C. bacteria were cultured on sterile polycarbonate membrane filters placed on LB agar plates and allowed to form a mature biofilm for 48 h. The biofilm was then exposed to BED or placebo for the following 24 h.

Energy Dispersive X-Ray Spectroscopy (EDS)

EDS elemental analysis of the Ag/ZN BED was performed in an environmental scanning electron microscope (ESEM, FEI XL-30) at 25 kV. A thin layer of carbon was evaporated onto the surface of the dressing to increase the conductivity.

Scanning Electron Microscopy

Biofilm was grown on circular membranes and was then fixed in a 4% formaldehyde/2% glutaraldehyde solution for 48 hours at 4° C., washed with phosphate-buffered saline solution buffer, dehydrated in a graded ethanol series, critical point dried, and mounted on an aluminum stub. The samples were then sputter coated with platinum (Pt) and imaged with the SEM operating at 5 kV in the secondary electron mode (XL 30S; FEG, FEI Co., Hillsboro, Oreg.).

Live/Dead Staining

The LIVE/DEAD BacLight Bacterial Viability Kit for microscopy and quantitative assays was used to monitor the viability of bacterial populations. Cells with a compromised membrane that are considered to be dead or dying stain red, whereas cells with an intact membrane stain green.

EPR Spectroscopy

EPR measurements were performed at room temperature using a Bruker ER 300 EPR spectrometer operating at X-band with a TM 110 cavity. The microwave frequency was measured with an EIP Model 575 source-locking microwave counter (EIP Microwave, Inc., San Jose, Calif.). The instrument settings used in the spin trapping experiments were as follows: modulation amplitude, 0.32 G; time constant, 0.16 s; scan time, 60 s; modulation frequency, 100 kHz; microwave power, 20 mW; microwave frequency, 9.76 GHz. The samples were placed in a quartz EPR flat cell, and spectra were recorded at ambient temperature (25° C.). Serial 1-min EPR acquisitions were performed. The components of the spectra were identified, simulated, and quantitated as reported. The double integrals of DEPMPO experimental spectra were compared with those of a 1 mM TEMPO sample measured under identical settings to estimate the concentration of superoxide adduct.

Quantification of mRNA and miRNA Expression

Total RNA, including the miRNA fraction, was isolated using Norgen RNA isolation kit, according to the manufacturers protocol. Gene expression levels were quantified with real-time PCR system and SYBR Green (Applied Biosystems) and normalized to nadB and proC as housekeeping genes. Expression levels were quantified employing the 2 (−ΔΔct) relative quantification method.

Glycerol-3-Phosphate Dehydrogenase Assay

The glycerol-3-phosphate dehydrogenase assay was performed using an assay kit from Biovision, Inc. following manufacturer's instructions. Briefly, cells ($\sim 1\times 10^6$) were homogenized with 200 µl ice cold GPDH Assay buffer for 10 minutes on ice and the supernatant was used to measure O.D. and GPDH activity calculated from the results.

Statistics

Control and treated samples were compared by paired t test. Student's t test was used for all other comparison of difference between means. $P<0.05$ was considered significant.

Ag/Zn BED Disrupts *P. aeruginosa* Biofilm

To validate the chemical composition of the dressing, we collected high resolution electron micrographs using an environmental scanning electron microscope. Our element maps indicate that silver particles are concentrated in the golden dots of the polyester cloth, while zinc particles are concentrated in the grey dots.

Figure 18A:
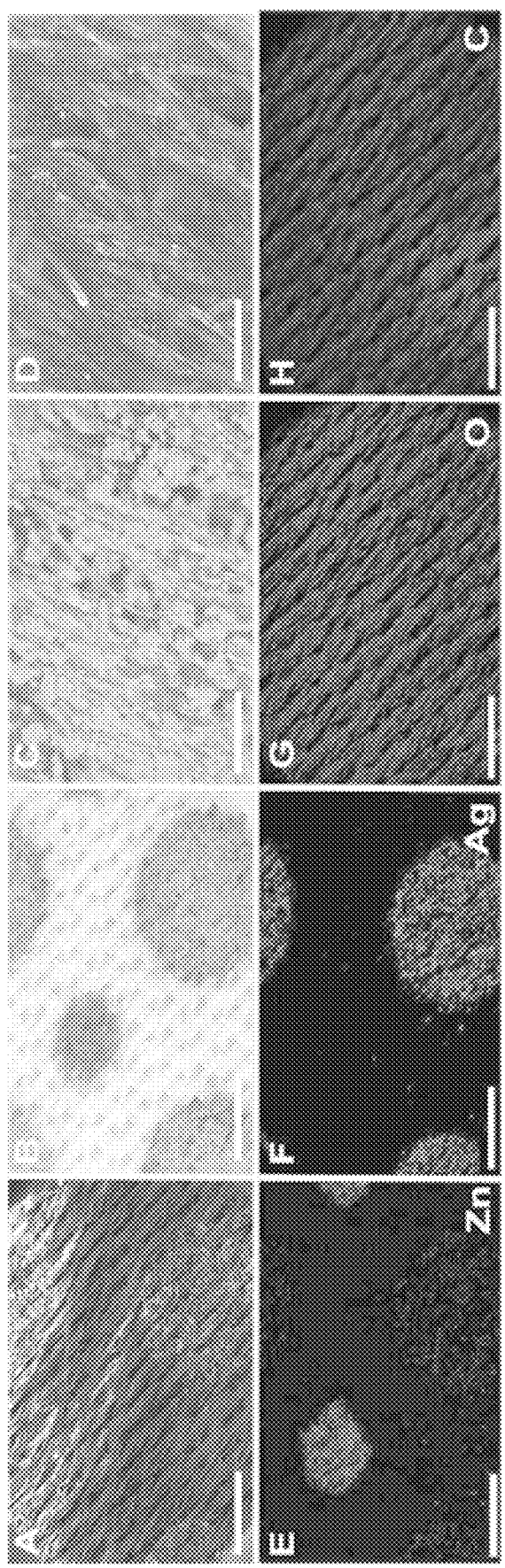
FIG. 18(A) is an Energy Dispersive X-ray Spectroscopy (EDS) analysis of Ag/Zn BED ("bioelectric device"; refers to an embodiment as disclosed herein).
Figure 18B:
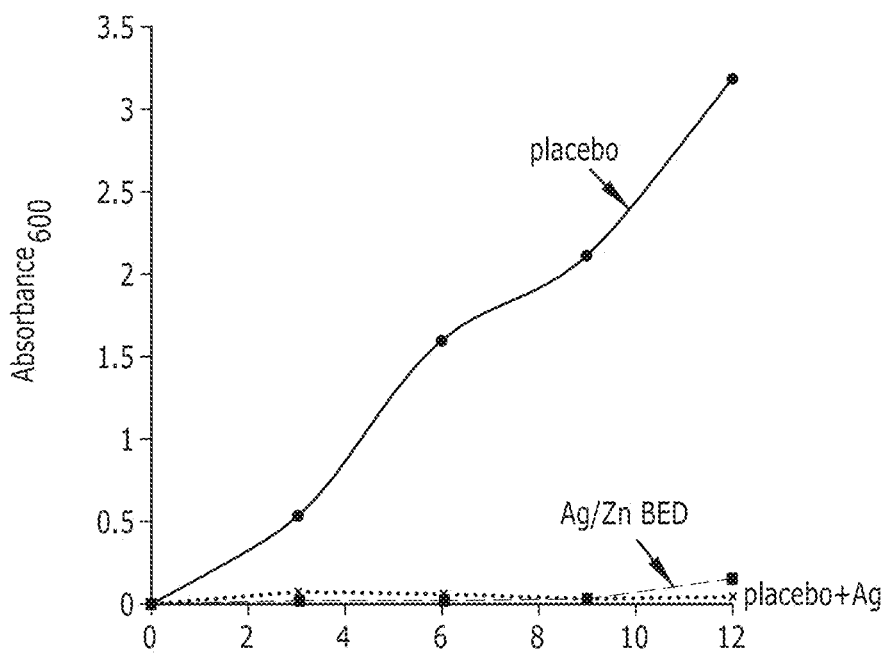
Figure 18C:
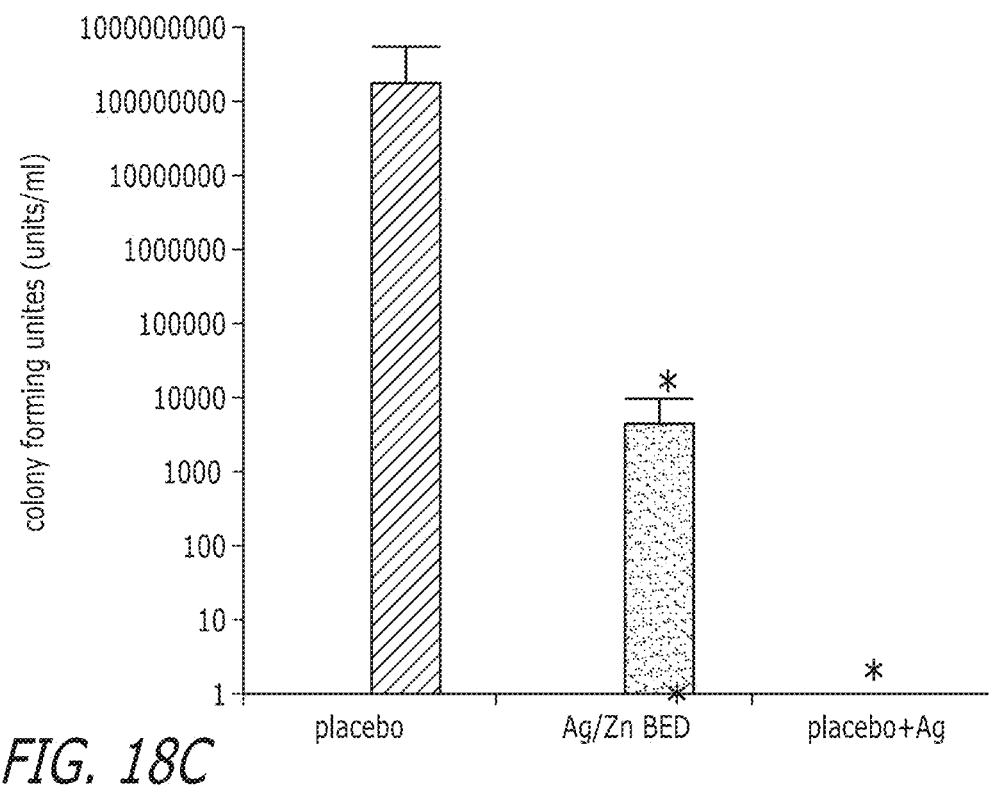
Figure 18D:
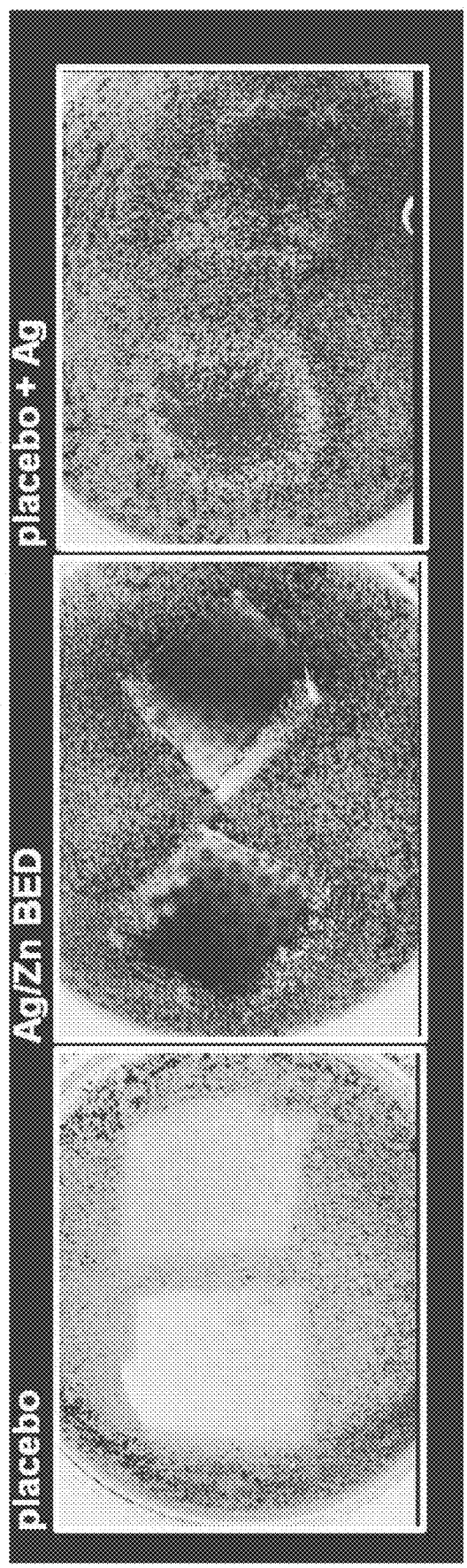

As illustrated in FIG. 18A, *P. aeruginosa* was grown in round bottom tubes in LB medium with continuous shaking and absorbance was measured by calculating optical density at 600 nm at different time points. It was observed that Ag/Zn BED and the control dressing with equal amount of silver inhibited bacterial growth (n=4) (FIG. 18B,C). When bacteria is grown in an agar plate with Ag/Zn BED dressing or placebo embedded in the agar, the zone of inhibition is clearly visible in the case of Ag/Zn BED thus demonstrating its bacteriostatic property, while placebo with silver dressing showed a smaller zone of inhibition, indicating the effect role of electric field as compared to topical contact. (FIG. 18D). However, as evident from scanning electron microscope images (FIG. 19); EPS staining (FIG. 20); and live/dead staining (FIG. 21), Ag/Zn BED disrupts biofilm much better while silver does not have any effect on biofilm disruption. Silver has been recognized for its antimicrobial properties for centuries. Most studies on the antibacterial efficacy of silver, with particular emphasis on wound healing, have been performed on planktonic bacteria. Silver ions, bind to and react with proteins and enzymes, thereby causing structural changes in the bacterial cell wall and membranes, leading to cellular disintegration and death of the bacterium. Silver also binds to bacterial DNA and RNA, thereby inhibiting the basal life processes.

Silver is effective against mature biofilms of *P. aeruginosa*, but only at a high silver concentration. A concentration of 5-10 µg/mL silver sulfadiazine has been reported to eradicate biofilm whereas a lower concentration (1 µg/mL) had no effect. Therefore, the concentration of silver in currently available wound dressings is much too low for treatment of chronic biofilm wounds. FIG. 18 shows PAO1 staining of the biofilm demonstrating the lack of elevated mushroom like structures in the Ag/Zn BED treated sample.

Ag/Zn BED Down-Regulates Quorum Sensing Genes

The pathogenicity of *P. aeruginosa* is attributable to an arsenal of virulence factors. The production of many of these extracellular virulence factors occurs only when the bacterial cell density has reached a threshold (quorum). Quorum sensing is controlled primarily by two cell-to-cell signaling systems, called las and rhl, which are both composed of a transcriptional regulator (LasR and RhlR, respectively) and an autoinducer synthase (LasI and RhlI, respectively). In *P. aeruginosa*, LasI produces 3OC12-HSL. LasR, then, responds to this signal and the LasR:3OC12-HSL complex activates transcription of many genes including rhlR, which encodes a second quorum sensing receptor, RhlR which binds to autoinducer C4-HSL produced by RhlI. RhlR:C4-HSL also directs a large regulon of genes. *P. aeruginosa* defective in QS is compromised in their ability to form biofilms. Quorum sensing inhibitors increase the susceptibility of the biofilms to multiple types of antibiotics.

To test the effect of the electric field on quorum sensing genes, we subjected the mature biofilm to the Ag/Zen BED or placebo for 12 hours and looked at gene expression levels. We selected an earlier time point, because by 24 hours, as in earlier experiments, most bacteria under Ag/Zn BED treatment were dead. We found a significant down regulation of lasR and rhlR (n=4, $p<0.05$). lasR transcription has been reported to weakly correlate with the transcription of lasA, lasB, toxA and aprA. We did not, however, find any significant difference in their expression levels at this time point, although we found them down regulated in the Ag/Zn BED treated samples at the 24 hour time point (data not shown). (FIG. 23).

Ag/Zn BED Represses the Redox Sensing Multidrug Efflux System in *P. aeruginosa*

Ag/Zn BED acts as a reducing agent and reduces protein thiols. One electron reduction of dioxygen $O_2$, results in the production of superoxide anion. Molecular oxygen (dioxygen) contains two unpaired electrons. The addition of a second electron fills one of its two degenerate molecular orbitals, generating a charged ionic species with single unpaired electrons that exhibit paramagnetism. Superoxide anion, which can act as a biological reductant and can reduce disulfide bonds, is finally converted to hydrogen peroxide is known to have bactericidal properties. Here, we used electron paramagnetic resonance (EPR) to detect superoxide directly upon exposure to the bioelectric dressing. Superoxide spin trap was carried out using DEPMPO (2-(diethoxyphosphoryl)-2-methyl-3,4-dihydro-2H-pyrrole 1-oxide) and ~1 µM superoxide anion production was detected upon 40 mins of exposure to Ag/Zn BED (FIG. 24). MexR and MexT are two multidrug efflux regulators in *P. aeruginosa* which uses an oxidation-sensing mechanism. Oxidation of both MexR and MexT results in formation of intermolecular disulfide bonds, which activates them, leading to dissociation from promoter DNA and de-repression of MexAB-oprM and MexEF-oprN respectively, while in a reduced state, they do not transcribe the operons. Induction of Mex operons leads not only to increased antibiotic resistance but also to repression of the quorum sensing cascades and several virulence factors. We observe down-regulation of the downstream Mex genes MexA, MexB, MexE and MexF (but not MexC and MexD) (n=4, $p<0.05$), in Ag/Zn BED treated samples, inactive forms of MexR and MexT in their reduced states. To confirm the reducing activity of the Ag/Zn BED, the experiments were repeated with 10 mM DTT and similar results were observed. (FIG. 25).

Ag/Zn BED Diminishes Glycerol-3-Phosphate Dehydrogenase Enzyme Activity

Electric fields can affect molecular charge distributions on many enzymes. Glycerol-3-phosphate dehydrogenase is an enzyme involved in respiration, glycolysis, and phospholipid biosynthesis and is expected to be influenced by external electric fields in *P. aeruginosa*. We observed significantly diminished glycerol-3-phosphate dehydrogenase enzyme activity by treating *P. aeruginosa* biofilm to the Ag/Zn BED for 12 hours (n=3). (FIG. 26).

Example 14

LLEC Influence on Biofilm Properties

In this study ten clinical wound pathogens associated with chronic wound infections were used for evaluating the anti-biofilm properties of a LLEC. Hydrogel and drip-flow reactor (DFR) biofilm models were employed for the efficacy evaluation of the wound dressing in inhibiting biofilms. Biofilms formed with *Acinetobacter baumannii*, *Corynebacterium amycolatum*, *Escherichia coli*, *Enterobacter aerogenes*, *Enterococcus faecalis* CI 4413, *Klebsiella pneumonia*, *Pseudomonas aeruginosa*, *Serratia marcescens*, *Staphylococcus aureus*, and *Streptococcus equi* clinical isolates were evaluated. For antimicrobial susceptibility testing of biofilms, $10^5$ CFU/mL bacteria was used in both biofilm models. For poloxamer hydrogel model, the LLECs (25 mm diameter) were applied directly onto the bacterial biofilm developed onto 30% poloxamer hydrogel and Muller-Hinton agar plates, and incubated at 37° C. for 24 h to observe any growth inhibition. In the DFR biofilm model, bacteria were deposited onto polycarbonate membrane as abiotic surface, and sample dressings were applied onto the membrane. The DFR biofilm was incubated in diluted trypticase soy broth (TSB) at room temperature for 72 h. Biofilm formations were evaluated by crystal violet staining under light microscopy, and anti-biofilm efficacy was demonstrated by reduction in bacterial numbers.

Example 15

Modulation of Mammalian Gene Expression and Enzyme Activity

Grown overnight in LB medium at 37° C., primary human dermal fibroblasts are cultured on sterile polycarbonate membrane filters placed on LB agar plates for 48 h. The cells are then exposed to BED or placebo for the following 24 h. BED represses the expression of glyceraldehyde 3-phosphate dehydrogenase. BED also down-regulates the activity of glyceraldehyde 3-phosphate dehydrogenase.

Example 16

Modulation of Insect Gene Expression and Enzyme Activity

Grown overnight in LB medium at 37° C., *drosophila* S2 cells are cultured on sterile polycarbonate membrane filters placed on LB agar plates for 48 h. The cells are then exposed to BED or placebo for the following 24 h. BED represses the expression of insect P450 enzymes. BED also down-regulates the activity of insect P450 enzymes.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method for reducing post-surgical infections comprising applying a stretchable device to an area where a surgical incision is to be made, then making the surgical incision, said device comprising an outer elastic layer and a substrate, said substrate comprising at least one slit perpendicular to a long axis of the device wherein said slit does not extend to the perimeter of the device, said substrate comprising a plurality of biocompatible electrodes configured to generate a low level electric current (LLEC) when exposed to a conductive fluid, wherein the biocompatible electrodes comprise a first array comprising a first pattern of microcells formed from a first conductive cathode material, and a second array comprising a second pattern of microcells formed from a second conductive anode material.

2. The method of claim 1, wherein the first array and the second array each comprise a separate discrete circuit, wherein each discrete circuit comprises a physical connection between the electrodes of each array.

3. The method of claim 2, further comprising a power source electrically connected to each array.

4. The method of claim 1, wherein the first array and the second array spontaneously generate a Low Level Electric Field (LLEF).

5. The method of claim 1, wherein said reducing post-surgical infections comprises reducing microorganism proliferation.

6. The method of claim 1, wherein said first conductive cathode material comprises silver.

7. The method of claim 1, wherein said second conductive anode material comprises zinc.

8. The method of claim 1, wherein said surgical site comprises the face.

9. The method of claim 8, wherein said surgical site comprises one of the eyelid, the ear, the lips, or the nose.

10. The method of claim 1, wherein said surgical site comprises one of the shoulder, the elbow, the wrist, the finger joints, the hip, the knee, the ankle, or the toe joints.

11. The method of claim 1, wherein said surgical site comprises the back or shoulder.

12. A method for accelerating a post-surgical healing process comprising applying a stretchable device to an area where a surgical incision is to be made, then making the surgical incision, said device comprising an outer elastic layer and a substrate, said substrate comprising at least one slit perpendicular to a long axis of the device wherein said slit does not extend to the perimeter of the device, said substrate comprising a plurality of biocompatible electrodes configured to generate a low level electric current (LLEC) when exposed to a conductive fluid, wherein the biocompatible electrodes comprise a first array comprising a first pattern of microcells formed from a first conductive cathode material, and a second array comprising a second pattern of microcells formed from a second conductive anode material.

13. The method of claim 12, wherein said accelerating the post-surgical healing process comprises increasing integrin accumulation.

* * * * *